US009220720B2

(12) United States Patent
Dudley, Jr.

(10) Patent No.: US 9,220,720 B2
(45) Date of Patent: *Dec. 29, 2015

(54) METHOD FOR AMELIORATING OR PREVENTING ARRHYTHMIC RISK ASSOCIATED WITH CARDIOMYOPATHY

(75) Inventor: Samuel C. Dudley, Jr., Chicago, IL (US)

(73) Assignees: U.S. DEPARTMENT OF VETERANS AFFAIRS, Washington, DC (US); THE BOARD OF TRUSTEES OF THE UNIV. OF ILLINOIS, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,790

(22) Filed: Jul. 18, 2012

(65) Prior Publication Data

US 2012/0288486 A1 Nov. 15, 2012

Related U.S. Application Data

(63) Continuation-in-part of application No. 12/929,786, filed on Feb. 16, 2011, now Pat. No. 9,114,151, which is a continuation-in-part of application No. 12/289,005, filed on Oct. 17, 2008, now Pat. No. 8,003,324.

(60) Provisional application No. 61/305,668, filed on Feb. 18, 2010, provisional application No. 60/960,883, filed on Oct. 18, 2007.

(51) Int. Cl.
*A61K 31/675* (2006.01)
*A61K 31/7084* (2006.01)
*A61K 31/662* (2006.01)

(52) U.S. Cl.
CPC ........... *A61K 31/7084* (2013.01); *A61K 31/662* (2013.01)

(58) Field of Classification Search
CPC ....................... A61K 31/662; A61K 31/7084
See application file for complete search history.

(56) References Cited

U.S. PATENT DOCUMENTS

| | | | |
|---|---|---|---|
| 5,668,114 A | 9/1997 | Birkmayer | |
| 5,849,732 A | 12/1998 | Suzuki et al. | |
| 6,339,073 B1 | 1/2002 | Pero | |
| 6,833,371 B2 | 12/2004 | Atkinson et al. | |
| 7,094,600 B2 | 8/2006 | Wang | |
| 7,226,950 B2 | 6/2007 | Choi et al. | |
| 8,003,324 B2 | 8/2011 | Dudley, Jr. | |
| 2004/0091477 A1 | 5/2004 | Haines et al. | |
| 2005/0202093 A1 | 9/2005 | Kohane et al. | |
| 2006/0281668 A1 | 12/2006 | Parobok et al. | |
| 2007/0212723 A1 | 9/2007 | Dudley et al. | |
| 2008/0032940 A1* | 2/2008 | Kalyanaraman et al. | 514/34 |
| 2008/0075666 A1 | 3/2008 | Dudley, Jr. et al. | |
| 2011/0144192 A1 | 6/2011 | Dudley, Jr. | |
| 2011/0288044 A1 | 11/2011 | Dudley, Jr. | |
| 2012/0289482 A1 | 11/2012 | Dudley, Jr. | |
| 2012/0308542 A1 | 12/2012 | Dudley, Jr. | |

FOREIGN PATENT DOCUMENTS

| | | |
|---|---|---|
| WO | WO 96/19225 A1 | 6/1996 |
| WO | WO 2007/098065 A1 | 8/2007 |
| WO | WO 2010/129964 A1 | 11/2010 |

OTHER PUBLICATIONS

Liu et al. Biophysical Society Meeting Abstracts, Jan. 2010, Biophysical Journal, Supplement p. 7a.*
Murphy et al., Annu. Rev. Pharmacol. Toxicol. 2007, 47:629-56.*
Alexis Biochemicals Catalog pp. 1-48, published Apr. 2007.*
Bardy GH, Lee KL, Mark DB, Poole JE, Packer DL, Boineau R, Domanski M, Troutman C, Anderson J, Johnson G, McNulty SE, Clapp-Channing N, Davidson-Ray LD, Fraulo ES, Fishbein DP, Luceri RM, Ip JH. Amiodarone or an implantable cardioverter-defibrillator for congestive heart failure. *N Engl J Med* 2005;352(3):225-37.
Kamphuis HCM, de Leeuw JRJ, Derksen R, Hauer RNW, Winnubst JAM. Implantable cardioverter defibrillator recipients: quality of life in recipients with and without ICD shock delivery. *Europace* 2003;5(4):381-9.
Thomas SA, Friedmann E, Kao CW, Inguito P, Metcalf M, Kelley FJ, Gottlieb SS. Quality of life and psychological status of patients withiImplantable cardioverter defibrillators. *Am J Crit Care* 2006;15(4):389-98.
Valdivia CR, Chu WW, Pu J, Foell JD, Haworth RA, Wolff MR, Kamp TJ, Makielski JC. Increased late sodium current in myocytes from a canine heart failure model and from failing human heart. *J Mol Cell Cardiol* 2005;38(3):475-83.
Ufret-Vincenty CA, Baro DJ, Lederer WJ, Rockman HA, Quinones LE, Santana LF. Role of sodium channel deglycosylation in the genesis of cardiac arrhythmias in heart failure. *J Biol Chem* 2001;276(30):28197-203.
Pu J, Boyden PA. Alterations of Na$^+$currents in myocytes from epicardial border zone of the infarcted heart. A possible ionic mechanism for reduced excitability and postrepolarization refractoriness. *Circ Res* 1997;81(1):110-9 (18 pgs), with supplement (15 pgs).
Baba S, Dun W, Boyden PA. Can PKA activators rescue Na$^+$channel function in epicardial border zone cells that survive in the infarcted canine heart? *Cardiovasc Res* 2004;64(2):260-7.
Shaw RM, Rudy Y. Ionic mechanisms of propagation in cardiac tissue: roles of the sodium and L-type calcium currents during reduced excitability and decreased gap junction coupling. *Circ Res* 1997;81(5):727-41 (22 pgs), with supplement (17 pgs).
Liu M, Sanyal S, Gao G, Gurung IS, Zhu X, Gaconnet G, Kerchner LG, Shang LL, Huang CLH, Grace A, London B, Dudley SC, Jr. Cardiac Na$^+$current regulation by pyridine nucleotides. *Circ Res* 2009;105(8):737-45, with supplement (16 pgs).

(Continued)

*Primary Examiner* — Doug Schultz
(74) *Attorney, Agent, or Firm* — Dinesh Agarwal, P.C.

(57) ABSTRACT

A method for reducing arrhythmic risk associated with cardiomyopathy includes administering a composition containing NAD$^+$ or a mitochondrial targeted antioxidant to an individual in need thereof.

21 Claims, 7 Drawing Sheets
(1 of 7 Drawing Sheet(s) Filed in Color)

(56) References Cited

OTHER PUBLICATIONS

Liu M, Liu H, Dudley SC, Jr. Reactive oxygen species originating from mitochondria regulate the cardiac sodium channel. *Circ Res* 2010;107(8):967-74, with supplement (10 pgs).
Aon MA, Cortassa S, Marban E, O'Rourke B. Synchronized whole cell oscillations in mitochondrial metabolism triggered by a local release of reactive oxygen species in cardiac myocytes. *J Biol Chem* 2003;278(45):44735-44, with supplement (9 pgs).
Di LF, Menabo R, Canton M, Barile M, Bernardi P. Opening of the mitochondrial permeability transition pore causes depletion of mitochondrial and cytosolic $NAD^+$ and is a causative event in the death of myocytes in postischemic reperfusion of the heart. *J Biol Chem* 2001;276(4):2571-5.
Silberman GA, Fan T-H, Liu H, Jiao Z, Xiao HD, Lovelock JD, Boulden B, Widder J, Fredd S, Bernstein KE, Wolska B, Dikalov S, Harrison DG, Dudley SC Jr. Uncoupled cardiac nitric oxide synthase mediates diastolic dysfunction. *Circulation* 2010;121(4):519-28, with supplement (21 pgs).
O'Connor DT, Rodrigo M, Simpson P. Isolation and culture of adult mouse cardiac myocytes. *Methods Mol Biol* 2007;357:271-96.
London B, Michalec M, Mehdi H, Zhu X, Kerchner L, Sanyal S, Viswanathan PC, Pfahnl AE, Shang LL, Madhusudanan M, Baty CJ, Lagana S, Aleong R, Gutmann R, Ackerman MJ, McNamara DM, Weiss R, Dudley SC, Jr. Mutation in Glycerol-3-Phosphate Dehydrogenase 1-Like Gene (GPD1-L) Decreases Cardiac $Na^+$ Current and Causes Inherited Arrhythmias. *Circulation* 2007;116(20):2260-8.
Landmesser U, Dikalov S, Price SR, McCann L, Fukai T, Holland S, Mitch WE, Harrison DG. Oxidation of tetrahydrobiopterin leads to uncoupling of endothelial cell nitric oxide synthase in hypertension. *J Clin Invest* 2003;111(8):1201-9.
Abriel H, Kass RS. Regulation of the voltage-gated cardiac sodium channel $Na_v$ 1.5 by interacting proteins. *Trends Cardiovasc Med* 2005;15(1):35-40.
Abriel H. Cardiac sodium channel $Na_v$1.5 and its associated proteins. *Arch Mal Coeur Vaiss* 2007;100(9):787-93.
Shibata EF, Brown TL, Washburn ZW, Bai J, Revak TJ, Butters CA. Autonomic regulation of voltage-gated cardiac ion channels. *J Cardiovasc Electrophysiol* 2006;17 Suppl 1:S34-S42.
Akai J, Makita N, Sakurada H, Shirai N, Ueda K, Kitabatake A, Nakazawa K, Kimura A, Hiraoka M. A novel SCN5A mutation associated with idiopathic ventricular fibrillation without typical ECG findings of Brugada syndrome. *FEBS Lett* 2000;479(1-2):29-34.
Brugada P, Brugada R, Brugada J. The Brugada syndrome. *Curr Cardiol Rep* 2000;2(6):507-14.
Makiyama T, Akao M, Tsuji K, Doi T, Ohno S, Takenaka K, Kobori A, Ninomiya T, Yoshida H, Takano M, Makita N, Yanagisawa F, Higashi Y, Takeyama Y, Kita T, Horie M. High risk for bradyarrhythmic complications in patients with Brugada syndrome caused by SCN5A gene mutations. *J Am Coll Cardiol* 2005;46(11):2100-6.
Zicha S, Maltsev VA, Nattel S, Sabbah HN, Undrovinas AI. Post-transcriptional alterations in the expression of cardiac $Na^+$ channel subunits in chronic heart failure. *J Mol Cell Cardiol* 2004;37(1):91-100.
Beswick RA, Zhang H, Marable D, Catravas JD, Hill WD, Webb RC. Long-term antioxidant administration attenuates mineralocorticoid hypertension and renal inflammatory response. *Hypertension* 2001;37(2):781-6.
Beswick RA, Dorrance AM, Leite R, Webb RC. NADH/NADPH oxidase and enhanced superoxide production in the mineralocorticoid hypertensive rat. *Hypertension* 2001;38(5):1107-11, with supplement (3 pgs).
Dikalova AE, Bikineyeva AT, Budzyn K, Nazarewicz RR, McCann L, Lewis W, Harrison DG, Dikalov SI. Therapeutic targeting of mitochondrial superoxide in hypertension. *Circ Res* 2010;107(1):106-16, with supplement (24 pgs).

Schreibmayer W, Dascal N, Lotan I, Wallner M, Weigl L. Molecular mechanism of protein kinase C modulation of sodium channel α-subunits expressed in Xenopus oocytes. *FEBS Lett* 1991;291(2):341-4.
Bruzzone S, Moreschi I, Guida L, Usai C, Zocchi E, De-áflora A. Extracellular $NAD^+$ regulates intracellular calcium levels and induces activation of human granulocytes. *Biochem J* 2006;393(3):697-704.
Romanello M, Padoan M, Franco L, Veronesi V, Moro L, D'Andrea P. Extracellular $NAD^+$ induces calcium signaling and apoptosis in human osteoblastic cells. *Biochem Biophys Res Commun* 2001;285(5):1226-31.
Bobalova J, Mutafova-Yambolieva VN. Activation of the adenylyl cyclase/protein kinase A pathway facilitates neural release of β-nicotinamide adenine dinucleotide in canine mesenteric artery. *Eur J Pharmacol* 2006;536(1-2):128-32.
Technikova-Dobrova Z, Sardanelli A, Speranza F, Scacco S, Signorile A, Lorusso V, Papa S. Cyclic adenosine monophosphate-dependent phosphorylation of mammalian mitochondrial proteins: enzyme and substrate characterization and functional role. *Biochemistry* 2010.40:13941-7.
Xie GH, Rah SY, Kim SJ, Nam TS, Ha KC, Chae SW, Im MJ, Kim UH. ADP-ribosyl cyclase couples to cyclic AMP signaling in the cardiomyocytes. *Biochem Biophys Res Commun* 2005;330(4):1290-8.
Zhang F, Jin S, Yi F, Xia M, Dewey WL, Li PL. Local production of $O_2^-$ by NAD(P)H oxidase in the sarcoplasmic reticulum of coronary arterial myocytes: cADPR-mediated $Ca^{2+}$ regulation. *Cell Signal* 2008;20(4):637-44.
Deng N, Zhang J, Zong C, Wang Y, Lu H, Yang P, Wang W, Young GW, Wang Y, Korge P, Lotz C, Doran P, Liem DA, Apweiler R, Weiss JN, Duan H, Ping P. Phosphoproteome analysis reveals regulatory sites in major pathways of cardiac mitochondria. *Mol Cell Proteomics* 2011;10(2):M110.000117 (14 pgs).
Kohlhaas M, Liu T, Knopp A, Zeller T, Ong MF, Böhm M, O'Rourke B, Maack C. Elevated cytosolic $Na^+$ increases mitochondrial formation of reactive oxygen species in failing cardiac myocytes. *Circulation* 2010;121(14):1606-13, with supplement (10 pgs).
Epstein AE, DiMarco JP, Ellenbogen KA, Estes NA, III, Freedman RA, Gettes LS, Gillinov AM, Gregoratos G, Hammill SC, Hayes DL, Hlatky MA, Newby LK, Page RL, Schoenfeld MH, Silka MJ, Stevenson LW, Sweeney MO, Smith SC, Jr., Jacobs AK, Adams CD, Anderson JL, Buller CE, Creager MA, Ettinger SM, Faxon DP, Halperin JL, Hiratzka LF, Hunt SA, Krumholz HM, Kushner FG, Lytle BW, Nishimura RA, Ornato JP, Page RL, Riegel B, Tarkington LG, Yancy CW. ACC/AHA/HRS 2008 Guidelines for Device-Based Therapy of Cardiac Rhythm Abnormalities: a report of the American College of Cardiology/American Heart Association Task Force on Practice Guidelines (Writing Committee to Revise the ACC/AHA/NASPE 2002 Guideline Update for Implantation of Cardiac Pacemakers and Antiarrhythmia Devices): developed in collaboration with the American Association for Thoracic Surgery and Society of Thoracic Surgeons. *Circulation* 2008;117(21):e350-e408, with correction(2 pgs).
Ruan Y, Liu N, Priori SG. Sodium channel mutations and arrhythmias. *Nat Rev Cardiol* 2009;6(5):337-48.
Bogdanov KY, Vinogradova TM, Lakatta EG. Sinoatrial nodal cell ryanodine ceceptor and Na+-Ca2+ exchanger: molecular partners in pacemaker regulation. Circ Res 2001;88:1254-8.
Lou Q, Fedorov VV, Glukhov AV, Moazami N, Fast VG, Efimov IR. Transmural heterogeneity and remodeling of ventricular excitation-contraction coupling in human heart failure / clinical perspective. Circulation 2011;123:1881-90, with supp. (12 pgs).
Fedorov W, Glukhov AV, Ambrosi CM, Kostecki G, Chang R, Janks D et al. Effects of KATP channel openers diazoxide and pinacidil in coronary-perfused atria and ventricles from failing and non-failing human hearts. J Mol Cell Cardiol 2011;51:215-25.
Laughner JI, Sulkin MS, Wu Z, Deng CX, Efimov IR. Three potential mechanisms for failure of high intensity focused ultrasound ablation in cardiac tissue/clinical perspective. Circ: Arrhythm Electrophysiol 2012;5:409-16.
Bayly P, KenKnight B, Rogers J, Hillsley R, Ideker R, Smith W. Estimation of conduction velocity vector fields from epicardial mapping data. IEEE Trans Biomed Eng 1998;45:563-71.

(56) References Cited

OTHER PUBLICATIONS

Glukhov AV, Fedorov VV, Kalish PW, Ravikumar VK, Lou Q, Janks D et al. Conduction remodeling in human end-stage nonischemic left ventricular cardiomyopathy/clinical perspective. Circulation 2012;125:1835-47, with supplement (27 pages).
Murphy E, Steenbergen C. Preconditioning: the mitochondrial connection. Annu Rev Physiol 2007;69:51-67,with content (3 pgs).
Barth E, Stämmler G, Speiser B, Schaper J. Ultrastructural quantitation of mitochondria and myofilaments in cardiac muscle from 10 different animal species including man. J Mol Cell Cardiol 1992;24:669-81.
Das DK, Maulik N. Mitochondrial function in cardiomyocytes: target for cardioprotection. Curr Opin Anaesthesiol 2005;18:77-82.
Duchen MR. Contributions of mitochondria to animal physiology: from homeostatic sensor to calcium signalling and cell death. J Physiol 1999;516:1-17.
Ide T, Tsutsui H, Kinugawa S, Utsumi H, Kang D, Hattori N et al. Mitochondrial electron transport complex I is a potential source of oxygen free radicals in the failing myocardium. Circ Res 1999;85:357-63.
Andrukhiv A, Costa ADT, West I, Garlid KD Opening mitoKATP increases superoxide generation from complex I of the electron transport chain. Am J Physiol Heart Circ Physiol 2006;291:H2067-H2074.
Eaton P. Protein thiol oxidation in health and disease: techniques for measuring disulfides and related modifications in complex protein mixtures. Free Radic Biol Med 2006;40:1889-99.
Winterbourn CC. Reconciling the chemistry and biology of reactive oxygen species. Nat Chem Biol 2008;4:278-86.
Santos CXC, Anilkumar N, Zhang M, Brewer AC, Shah AM. Redox signaling in cardiac myocytes. Free Radic Biol Med 2011;50:777-93.
Lovelock JD, Monasky MM, Jeong EM, Lardin HA, Liu H, Patel BG et al. Ranolazine improves cardiac diastolic dysfunction through modulation of myofilament calcium sensitivity. Circ Res 2012;110:841-50, with supp. (16 pgs).
Zhou J, Shin HG, Yi J, Shen W, Williams CP, Murray KT. Phosphorylation and putative ER retention signals are required for protein kinase A-mediated potentiation of cardiac sodium current. Circ Res 2002;91:540-6, with supp. (1 pg).
Tateyama M, Kurokawa J, Terrenoire C, Rivolta I, Kass RS. Stimulation of protein kinase C inhibits bursting in disease-linked mutant human cardiac sodium channels. Circulation 2003;107:3216-22.
Sovari AA, Rutledge CA, Jeong E-M, Dolmatova E, Arasu D, Liu H, Vandani N, Gu L, Zandieh S, Xiao L, Bonini MG, Duffy HS, Dudley SC. Mitochondria-Targeted Antioxidant Therapy Prevents Connexin 43 Remodeling and Sudden Death Caused by Renin-Angiotensin System Activation. Circulation. 2012; 126: A19711 (3 pages).
Sovari AA, Jeong EM, Zandieh S, Gu L, Iravanian S, Bonini M, Dudley SC. Mitochondria-Targeted Antioxidant Therapy Prevents Angiotensin II Medicated Connexin 43 Remodeling and Sudden Arrhythmic Death. Circulation, vol. 124 (21 Meeting Abs.) Supp. 1, Nov. 22, 2011. Abstract 15801 (1 pg).
Brugada P, Brugada J. Right bundle branch block, persistent ST segment elevation and sudden cardiac death: a distinct clinical and electrocardiographicsyndrome. A multicenter report. J Am Coll Cardiol. 1992;20:1391-1396.
Kadish, A. et al. 2006. Patients with recently diagnosed nonischemic cardiomyopathy benefit from implantable cardioverter-defbrillators. J. Am Coll. Cardiol. 47:2477-2482.
Amin AS, Verkerk AO, Bhuiyan ZA, Wilde AAM, Tan HL. Novel Brugada syndrom-causing mutation in ion-conducting pore of cardiac Na_channel does not affect ion selectivity properties. Acta Physiol Scand. 2005;185:291-301.
Baroudi G, Napolitano C, Priori SG, Del Bufalo A, Chahine M. Loss of function associated with novel mutations of the SCN5A gene in patients with Brugada syndrome. Can J Cardiol. 2004;20:425-430.
Baroudi G, Acharfi S, Larouche C, Chahine M. Expression and Intracellular localization of an SCN5A double mutant R1232W/T1620M implicated in Brugada syndrome. Circ Res. 2002;90:e11-e16.
Baroudi G, Pouliot V, Denjoy I, Guicheney P, Shrier A, Chahine M. Novel mechanism for Brugada syndrome: Defective surface localization of an SCN5A mutant (R1432G). Circ Res. 2001;88:e78-e83.
Vatta M, Dumaine R, Antzelevitch C, Brugada R, Li H, Bowles NE, Nademanee K, Brugada J, Brugada P, Towbin JA. Novel mutations in domain I of SCN5A cause Brugada syndrome. Mol Genet Metab. 2002;75:317-324.
London B, Michalec M, Mehdi H, Zhu X, Kerchner L, Sanyal S, Viswanathan PC, Pfahnl AE, Shang LL, Madhusudanan M, Baty CJ, Lagana S, Aleong R, Gutmann R, Ackerman MJ, McNamara DM, Weiss R, Dudley SC Jr. Mutation in glycerol-3-phosphate dehydrogenase 1-like gene (GPD1-L) decreases cardiac Na_current and causes inherited arrhythmias. Circulation. 2007;116:2260-2268.
Van Norstrand DW, Valdivia CR, Tester DJ, Ueda K, London B, Makielski JC, Ackerman MJ. Molecular and functional characterization of novel glycerol-3-phosphate dehydrogenase 1 like gene (GPD1-L) mutations in sudden infant death syndrome. Circulation. 2007;116:2253-2259.
Shen, W. et al. 2006. Involvement of glycerol-3-phosphate dehydrogenase in modulating the NADH/NAD + ratio provides evidence of a mitochondrial glycerol-3-phosphate shuttle in Arabidopsis. Plant Cell. 18:422-441.
Papadatos GA, Wallerstein PMR, Head CEG, Ratcliff R, Brady PA, Benndorf K, Saumarez RC, Trezise AEO, Huang CLH, Vandenberg JI, Colledge WH, Grace AA. Slowed conduction and ventricular tachycardia after targeted disruption of the cardiac sodium channel gene SCN5a. Proc Natl Acad Sci U S A. 2002;99:6210-6215.
Knollmann BC, Schober T, Petersen AO, Sirenko SG, Franz MR. Action potential characterization in intact mouse heart: steady-state cycle length dependence and electrical restitution. Am J Physiol Heart Circ Physiol. 2007;292:H614-H621.
Killeen MJ, Thomas G, Gurugn IS, Goddard CA, Fraser JA, Mahaut-Smith MP, Colledge WH, Grace AA, Huang CLH. Arrhythmogenic mechanisms in the isolated perfused hypokalaemic murine heart. Acta Physiol. 2007;189:33-46.
Zalba, G. et al. 2000. Vascular NADH/NADPH oxidase is involved in enhanced superoxide production in spontaneously hypertensive rats. Hypertension. 35:1055-1061.
Javesghani, D. et al. 2002. Molecular characterization of a superoxide-generating NAD(P)H oxidase in the ventilator muscles. Am. J. Respir. Crit. Care Med. 165: 412-418.
Zicha, S. Maltsev, V.A., Nattel, S., Sabbah, H.N. and Undrovinas, A.L. 2004. Posttranscriptional alterations in the expression of cardiac Na+ channel subunits in chronic heart failure. J. Mol. Cell. Cardiol. 37: 91-100.
Schreibmayer W, Dascal N, Lotan I, Wallner M, Weigl L. Molecular mechanism of protein kinase C modulation of sodium channel _-subunits expressed in Xenopus oocytes. FEBS Lett. 1991;291:341-344.
Ward, C.A., and Giles, W.R. 1997. Ionic mechanism of the effects of hydrogen peroxide in rat ventricular myocytes. J. Physiol. 500: 631-642.
Takeishi, Y., Jalili, T., Ball, N.A. and Walsh, R.A. 1999. Responses of cardiac protein kinase C isoforms to distinct pathological stimuli are differently regulated. Circ. Res. 85: 264-271.
Sharma, A. and Singh, M. 2001. Protein kinase C activation and cardioprotective effect of preconditioning with oxidative stress in isolated rat heart. Mol. Cell. Biochem. 219: 1-6.
Brawn, M.K., Chiou, W.J. and Leach, K.L. 1995. Oxidant-induced activation of protein kinase C in UC11Mg cells. Free Radic. Res. 22: 23-37.
Pfahnl AE, Viswanathan PC, Weiss R, Shang LL, Sanyal S, Shusterman V, Kornblit C, London B, Dudley SC Jr. A sodium channel pore mutation causing Brugada syndrome. Heart Rhythm. 2007;4:46-53.
Kyndt, F. et al. 2001. Novel SCN5A mutation leading either to isolated cardiac conduction defect or Brugada syndrome in a large French family. Circulation. 104:3081-3086.
Tipparaju SM, Saxena N, Liu SQ, Kumar R, Bhatnagar A. Differential regulation of voltage-gated K_channels by oxidized and reduced pyridine nucleotide coenzymes. Am J Physiol Cell Physiol. 2005;288: C366-C376.

(56) References Cited

OTHER PUBLICATIONS

Tipparaju SM, Liu SQ, Barski OA, Bhatnagar A. NAPH binding to _-subunit regulates inactivation of voltage-gated K_channels. *Biochem Biophys Res Commun.* 2007;359:269-276.

Heiner I, Eisfeld J, Halaszovich CR, Wehage E, Jüngling E, Zitt C Lückhoff A. Expression profile of the transient receptor potential (TRP) family in neutrophil granulocytes: evidence for currents through long TRP channel 2 induced by ADP-ribose and NAD. *Biochem J.* 2003;371: 1045-1053.

Herson PS, Dulock KA, Ashford ML. Characterization of a nicotinamideadenine dinucleotide-dependent cation channel in the CRI-G1 rat insulinoma cell line. *J. Physiol.* 1997;505:65-76.

Alvarez J, Camaleno J, Garcia-Sancho J, Herreros B. Modulation of Ca2_-dependent K_transport by modifications of the NAD_/NADH ratio in inact human red cells. *Biochim Biophys Acta.* 1986;856: 408-411.

Zima AV, Copello JA, Blatter LA. Effects of cytosolic NADH/NAD_ levels reticulum Ca2_release in permeabilized rat ventricular myocytes. *J Physiol.* 2004;555:727-741.

Park MK, Lee SH, Ho WK, Earm YE. Redox agents as a link between hypoxia and the responses of ionic channels in rabbit pulmonary vascular smooth muscle. *Exp Physiol.* 1995;80:835-842.

Aon MA, Cortassa S, Marban E, O'Rourke B. Synchronized whole cell oscillations in mitochondrial metabolism triggered by a local release of reactive oxygen species in cardiac myocytes. *J Biol Chem.* 2003;278: 44735-44744.

Di LF, Menabo R, Canton M, Barile M, Bernardi P. Opening of the mitochondrial permeability transition pore causes depletion of mitochondrial and cytosolic NAD_and is a causative event in the death of myocytes in postischemic reperfusion of the heart. *J Biol Chem.* 2001; 276:2571-2575.

Choudhary G, Dudley SC Jr. Heart failure, oxidative stress, and ion channel modulation. *Congest Heart Fail.* 2002;8:148-155.

Pillai JB, Isbatan A, Imai Si, Gupta MP. Poly(ADP-ribose) polymerase-1-dependent cardiac myocyte cell death during heart failure is mediated by NAD_depletion and reduced Sir2_ deacetylase activity. *J Biol Chem.* 2005;280:43121-43130.

Dzhanashiya PK, Vladytskaya OV, Salibegashvili NV. Efficiency and mechanisms of the antioxidant effect of standard therapy and refracterin in the treatment of chronic heart failure in elderly patients with postinfarction cardiosclerosis. *Bull Exp Biol Med.* 2004;138:412-414.

Shang LL, Pfahnl AE, Sanyal S, Jiao Z, Allen J, Banach K, Fahrenbach J, Weiss D, Taylor WR, Zafari AM, Dudley SC Jr. Human heart failure is associated with abnormal C-terminal splicing variants in the cardiac sodium channel. *Circ Res.* 2007;101:1146-1154, and Online Supplement (pp. 1-10).

Makielski JC, Farley A. Na_current in human ventricle: implications for sodium loading and homeostasis. *J Cardiovasc Electrophysiol.* 2006;17: S15-S20.

Valdivia CR, Chu WW, Pu J, Foell JD, Haworth RA, Wolff MR, Kamp TJ, Makielski JC. Increased late sodium current in myocytes from a canine heart failure model and from failing human heart. *J Mol Cell Cardiol.* 2005;38:475-483.

Ajiro Y, Hagiwara N, Kasanuki H. Assessment of markers for idendifying patients at risk for life-threatening arrhythmic events in Brugada syndrome. *J Cardiovasc Electrophysiol.* 2005;16:45-51.

Gellens et al. Primary Structure and Functional Expression of the Human Cardiac Tetrodotoxin-Insensitive Voltage-Dependent Sodium-Channel. *Proceedings of the National Academy of Sciences of the United States of America* 89, 554-558 (1992).

Wang et al. Genomic organization of the human SCN5A gene encoding the cardiac sodium channel. *Genomics* 34, 9-16 (1996).

George et al. Assignment of the human heart tetrodotoxin-resistant voltage-gated Sodium channel alpha-subunit gene (SCN5A) to band 3p21. *Cytogenet. Cell Genet.* 68, 67-70 (1995).

Schott et al. Cardiac conduction defects associate with mutations in SCN5A. *Nat. Genet.* 23, 20-21 (1999).

Tan et al. A calcium sensor in the sodium channel modulates cardiac excitability. *Nature* 415, 442-447 (2002).

Zubay, Biochemistry, Chapter 10, part II Carbohydrate metabolism and chemical energy, p. 400-403 (1984).

Remington's Pharmaceutical Sciences, Mace Publishing Company, Philadelphia, Pa., 17th ed. (1985).

Alings, M. and Wilde A. "Brugada" Syndrome: Clinical Data and Suggested Pathophysiological Mechanism. *Circulation* 1999; 99:666-673.

Brugada J, Brugada R, Antzelevitch C et al. Long-term follow-up of individuals with the electrocardiographic pattern of right bundle-branch block and ST-segment elevation in precordial leads V1 to V3. *Circulation.* 2002;105:73-78.

Zhou, M. Diwu Z., Panchuk-Voloshina, N. and Haugland. A Stable Nonfluorescent Derivative of Resorufin for the Fluorometric Determination of Trace Hydrogen Peroxide: Applications in Detecting the Activity of Phagocyte NADPH Oxidase and Other Oxidases. *Analytical Biochemistry* 253 (1997) 162-168.

Mohanty, J.G., Jaffe, J.S., Schulman, E.S. and Raible, D.G.. A Highly Sensitive Fluorescent Micro-Assay of H2O Release from Activated Human Leukocytes Using a Dihydroxyphenoxazine Derivative. *Journal of Immunological Methods* 202 (1997) 133-141.

Liu M, Sanyal S, Gao G, Gurung IS, Zhu X, Gaconnet G, Kerchner LJ, Shang LL, Huang CLH, Grace A, London B, Dudley SC, Jr. Cardiac Na+ current regulation by pyridine nucleotides. *Circ Res.* 2009; 105:737-45, Supplemental Material (pp. 1-8), and Author manuscript Cir Res Oct. 2009; 105(8):737-745.

Shaw RM, Rudy Y. Ionic mechanisms of propagation in cardiac tissue: roles of the sodium and L-type calcium currents during reduced excitability and decreased gap junction coupling. *Circ Res.* 1997; 81:727-41.

Shimizu W, Aiba T, Kamakura S. Mechanisms of disease: current understanding and future challenges in Brugada syndrome. *Nat Clin Pract Cardiovasc Med.* 2005; 2:408-14.

Andrukhiv A, Costa ADT, West I, Garlid KD. Opening of mitoK$_{ATP}$ increases superoxide generation from complex I of the electron transport chain. *Am J Physiol Heart Circ Physiol.* 2006; 291:H2067-H2074.

Ide T, Tsutsui H, Kinugawa S, Utsumi H, Kang D, Hattori N, Uchida K, Arimura Ki, Egashira K, Takeshita A. Mitochondrial electron transport complex I is a potential source of oxygen free radicals in the failing myocardium. *Circ Res.* 1999; 85:357-63.

Mallet Z, Philip I, Lebret M, Chatel D, Maclouf J, Tedgui A. Elevated levels of 8-iso-prostaglandin F2a in pericardial fluid of patients with heart failure : a potential role for in vivo oxidant stress in ventricular dilatation and progression to heart failure. *Circulation.* 1998; 97:1536-9.

Hill MF, Singal PK. Right and left myocardial antioxidant responses during heart failure subsequent to myocardial infarction. *Circulation.* 1997; 96:2414-20 (11 pages).

Dhalla AK, Singal PK. Antioxidant changes in hypertrophied and failing guinea pig hearts. *Am J Physiol Heart Circ Physiol.* 1994; 266:H1280-H1285.

Brady N, Hamacher-Brady A, Westerhoff H, Gottlieb R. A wave of reactive oxygen species (ROS)-induced ROS release in a sea of excitable mitochondria. *Antioxid Redox Signal.* 2006; 8:1651-65.

Zorov DB, Filburn CR, Klotz LO, Zweier JL, Sollott SJ. Reactive oxygen species (ROS)-induced ROS release: a new phenomenon accompanying induction of the mitochondrial permeability transition in cardiac myocytes. *J Exp Med.* 2000; 192:1001-14.

Costa ADT, Pierre SV, Cohen MV, Downey JM, Garlid KD. cGMP signalling in pre- and post-conditioning: the role of mitochondria. *Cardiovasc Res.* 2008; 77:344-52.

Ogbi M, Chew CS, Pohl J, Stuchlik O, Ogbi S, Johnson JA. Cytochrome c oxidase subunit IV as a marker of protein kinase Ce function in neonatal cardiac myocytes: implications for cytochrome c oxidase activity. *Biochem J.* 2004; 382:923-32.

Clarke SJ, McStay GP, Halestrap AP. Sanglifehrin A Acts as a Potent Inhibitor of the Mitochondrial Permeability Transition and Reperfusion Injury of the Heart by Binding to Cyclophilin-D at a Different Site from Cyclosporin A. *J Biol Chem* 2002;277:34793-9.

Sato T, O'Rourke B, Marban E. Modulation of mitochondrial ATP-dependent K+ channels by protein kinase C. *Circ Res.* 1998; 83:110-4.

(56) References Cited

OTHER PUBLICATIONS

O'Rourke B. Evidence for mitochondrial $K^+$ channels and their role in cardioprotection. *Circ Res.* 2004; 94:420-32, and Supplement (pp. 1-6).

Chen, Q, Vazquez E, Moghaddas S, Hoppel C, Lesnefsky E. Production of reactive oxygen species by mitochondria. *J Biol Chem.* 2003; 278:36027-31.

Akar FG, Aon MA, Tomaselli GF, O'Rourke B. The mitochondrial origin of postischemic arrhythmias. *J Clin Invest.* 2005; 115:3527-35.

Murphy MP. How mitochondria produce reactive oxygen species. *Biochem J.* 2009; 417:1-13.

O'Rourke B, Ramza B, Marban E. Oscillations of membrane current and excitability driven by metabolic oscillations in heart cells. *Science.* 1994; 265:962-6.

Murray KT, Hu N, Daw JR, Shin HG, Watson MT, Mashburn AB, George AL Jr. Functional effects of protein kinase C activation on the human cardiac Na_channel. *Circ Res.* 1997;80:370-376.

Zhou J, Yi J, Hu N, George AL Jr, Murray KT. Activation of protein kinase A modulates trafficking of the human cardiac soduim channel in Xenopus oocytes. *Circ Res.* 2000;87:33-38.

Hallaq et al. Quantitation of protein kinase A-mediated trafficking of cardiac sodium channels in living cells. Cardiovascular Research 72 (2006) 250-261.

Zhou J, Shin HG, Yi J, Shen W, Williams CP, Murray KT. Phosphorylation and putative ER retention signals are required for protein kinase A-mediated potentiation of cardiac sodium current. *Circ Res.* 2002;91: 540-546.

Zhang F, Jin S, Yi F, Xia M, Dewey WL, Li PL. Local production of O2 by NAD(P)H oxidase in the sarcoplasmic reticulum of coronary arterial myocytes: cADPR-mediated Ca2_regulation. *Cell Signal.* 2008;20: 637-644.

Nitti et al. PKC signaling in oxidative hepatic damage. Molecular Aspects of Medicine 29 (2008) 36-42.

Bruzzone et al. Extracellular NAD+ regulates intracellular calcium levels and induces activation of human granulocytes. Biochem. J. (2006) 393,697-704.

Romanello et al. Extracellular NAD1 Induces Calcium Signaling and Apoptosis in Human Osteoblastic Cells. Biochemical and Biophysical Research Communications 285, 1226-1231 (2001).

Budas & Mochly-Rosen. Mitochondrial protein kinase Cε (PKCε): emerging role in cardiac protection from ischaemic damage. Biochemical Society Transactions (2007) vol. 35, part 5, 1052-1054.

Silberman GA, Fan T-H, Liu H, Jiao Z, Xiao HD, Lovelock JD, Boulden B, Widder J, Fredd S, Bernstein KE, Wolska B, Dikalov S, Harrison DG, Dudley SCJr. Uncoupled cardiac nitric oxide synthase mediates diastolic dysfunction. *Circulation.* 2010; 121:519-28, and Supp. Data (21 pp.).

Sorescu D, Weiss D, Lassegue B, Clempus RE, Szocs K, Sorescu GP, Valppu L, Quinn MT, Lambeth JD, Vega JD, Taylor WR, Griendling KK. Superoxide production and expression of Nox family proteins in human atherosclerosis. *Circulation.* 2002; 105:1429-35.

Pacher P, Nivorozhkin A, Szabo C. Therapeutic effects of xanthine oxidase inhibitors: Renaissance half a century after the discovery of allopurinol. *Pharmacol Rev.* 2006; 58:87-114.

Kobayashi K, Neely JR. Control of maximum rates of glycolysis in rat cardiac muscle. *Circ Res.* 1979; 44:166-75.

Li Q, Hwang YC, Ananthakrishnan R, Oates PJ, Guberski D, Ramasamy R. Polyol pathway and modulation of ischemia-reperfusion injury in Type 2 diabetic BBZ rat hearts. *Cardiovasc Diabetol.* 2008; 7:33-44 (11 pages).

Moir AM, Zammit VA. Insulin-independent and extremely rapid switch in the partitioning of hepatic fatty acids from oxidation to esterification in starved-refed diabetic rats. *Biochem J.* 1995; 305:953-8.

van Raam B, Sluiter W, de Wit E, Roos D, Verhoeven A, Kuijpers T. Mitochondrial membrane potential in human neutropils is maintained by complex III activity in the absence of supercomplex organisation. *PLoS ONE.* 2008; 3:e2013 (12 pages).

Liang HL, Arsenault J, Mortensen J, Park F, Johnson CP, Nilakanta V. Partial attenuation of cytotoxicity and apoptosis by SOD1 in ischemic renal epithelial cells. *Apoptosis.* 2009; 14:1176-89.

Dikalova AE, Bikineyeva AT, Budzyn K, Nazarewicz RR, McCann L, Lewis W, Harrison DG, Dikalov SI. Therapeutic targeting of mitochondrial superoxide in hypertension. *Circ Res.* 2010; 107:106-16, and Online Supp. (12 pages).

Murphy E, Steenbergen C. Preconditioning: the mitochondrial connection. *Annu Rev Physiol.* 2007; 69:51-67.

Barth E, Stämmler G, Speiser B, Schaper J. Ultrastructural quantitation of mitochondria and myofilaments in cardiac muscle from 10 different animal species including man. *J Mol Cell Cardiol.* 1992; 24:669-81.

Boveris A, Oshino N, Chance B. The cellular production of hydrogen peroxide. *Biochem J.* 1972; 128:617-630.

Batandier C, Fontaine E, Keriel C, Leverve X. Determination of mitochondrial reactive oxygen species: methodological aspects. *J Cell Mol Med.* 2002; 6:175-87.

Panov A, Schonfeld P, Dikalov S, Hemendinger R, Bonkovsky HL, Brooks BR. The Neuromediator glutamate, through specific substrate interactions, enhances mitochondrial ATP production and reactive oxygen species generation in monsynaptic brain mitochondria. *J Biol Chem.* 2009; 284:14448-56.

Han D, Antunes F, Canali R, Rettori D, Cadenas E. Voltage-dependent anion channels control the release of the superoxide anion from mitochondria to cytosol. *J Biol Chem.* 2003; 278:5557-63.

Brown D, Aon MA, Akar FG, Liu T, Sorarrain N, O'Rourke B. Effects of 4'-chlorodiazepam on cellular excitation-constraction coupling and ischaemia-reperfusion injury in rabbit heart. *Cardiovasc Res.* 2008; 79:141-9.

Valdivia CR, Ueda K, Ackerman MJ, Makielski JC, GPD1L links redox state to cardiac excitability by PKC-dependent phosphorylation of the sodium channel SCN5A. *AJP—Heart and Circulatory Physiology.* 2009; 297:H1446-H1452.

Zelent B, Troxler T, Vanderkooi JM. Temperature dependence for fluorescence of β-NADH in glycerol/water solution and in trehalose/sucrose glass. *Journal of Fluorescence.* 2007; 17:37-42.

Liu M, Gaconnet G, London B, Dudley, Jr. S.C. A Central Role of Mitochondria in the Regulation of Sodium Current. Presentation at the Cardiac Electrophysiology Society, Orlando, Florida (Nov. 14, 2009) (1 page).

Yang H, Yang T, Baur JA, Perez E, Matsui T, Carmona JJ, Lamming D, Souza-Pinto NC, Bohr VA, Rosenzweig A, de Cabo R, Sauve A, Sinclair DA. Nutrient-sensitive mitochondrial NAD_levels dictate cell survival. *Cell.* 2007;130:1095-1107.

Lin SJ, Guarente L. Nicotinamide adenine dinucleotide, a metabolic regulator of transcription, longevity and disease. *Curr Opin Cell Biol.* 2003;15:241-246.

Herbert JM, Augereau JM, Gleye J, Maffrand JP. Chelerythrine is a potent and specific inhibitor of protein kinase C. *Biochem Biophys ResCommun.* 1990;172:993-999.

Chao MD, Chen IS, Cheng JT. Inhibition of protein kinase C translocation from cytosol to membrane by chelerythrine. *Planta Med.* 1998;64: 662-663.

Frohnwieser B, Chen L, Schreibmayer W, Kallen R. Modulation of the human cardiac sodium channel alpha-subunit by cAMP-dependent protein kinase and the responsible sequence domain. *J Physiol* (London). 1997;498:309-318.

Glass DB, Lundquist LJ, Katz BM, Walsh DA. Protein kinase inhibitor-(6-22)-amide peptide analogs with standard and nonstandard amino acid substitutions for phenylalanine 10. Inhibition of cAMP-dependent protein kinase. *J Biol Chem.* 1989;264:14579-14584.

Shin HG, Murray KT. Conventional protein kinase C isoforms and cross-activation of protein kinase A regulate cardiac Na_current. *FEBS Lett.* 2001;495:154-158.

Biswas S, DiSilvestre D, Tian Y, Halperin VL, Tomaselli GF. Calciummediated dual-mode regulation of cardiac sodium channel gating. *Circ Res.* 2009;104:870-878, and Supp. Material (10 pages).

Casini S, Verkerk AO, van Borren MM, van Ginneken AC, Veldkamp MW, de Bakker JM, Tan HL. Intracellular calcium modulation of voltage-gated sodium channels in ventricular myocytes. *Cardiovasc Res.* 2009;81:72-81.

(56) References Cited

OTHER PUBLICATIONS

Brisson D, Vohl M, St Pierre J, Hudson T, Gaudet D. Glycerol: a neglected variable in metabolic process? *Bioessays*. 2001;23.6:534-542.

Antzelevitch C, Brugada P, Borggrefe M, et al. Brugada syndrome: report of the second consensus conference: endorsed by the Heart Rhythm Society and the European Heart Rhythm Association. *Circulation*. 2005; 111:659-670.

Brugada J, Brugada P. Further characterization of the syndrome of right bundle branch block, ST segment elevation, and sudden cardiac death. *J Cardiovasc Electrophysiol*. 1997; 8:325-331.

Grant AD. Electrophysiological basis and genetics of Brugada syndrome. *J Cardiovasc Electrophysiol*. 2005; 16:S3-7.

Chen Q, Kirsch GE, Zhang 0, et al. Genetic basis and molecular mechanism for idiopathic ventricular fibrillation. *Nature*. 1998; 392:293-296.

Priori SG, Napolitano C, Gasparini M, et al. Clinical and genetic heterogeneity of right bundle branch block and ST-segment elevation syndrome: A prospective evaluation of 52 families. *Circulation*. 2000; 102:2509-2515.

Valdivia CR, Tester OJ, Rok BA, et al. A trafficking defective, Brugada syndromecausing SCNSA mutation rescued by drugs. *Cardiovasc Res*. 2004; 62:53-62.

Brugada R, Brugada J, Antzeievitch G, et al. Sodium channel blockers identify risk for sudden death in patients with ST-segment elevation and right bundle branch block but structurally normal hearts. *Circulation*. 2000; 101:510-515.

Pollevick GO, Schimpf R, Aizawa Y, et al. Loss of function in calcium channel activity secondary to a mutation in CACNB2b modulates the clinical manifestation of a combined Brugada syndrome-hort aT phenotype. *Circulation*. 2006; 114:11-193 (Abstract—3 pages).

Yan GX, Antzelevitch C. Cellular basis for the Brugada syndrome and other mechanisms of arrhythmogenesis associated with ST-segment elevation. *Circulation*. 1999; 100:1660-1666.

Weiss R, Barmada MM, Nguyen T, et al. Clinical and molecular heterogeneity in the Brugada syndrome: a novel gene locus on chromosome 3. *Circulation*. 2002;105:707-713.

Walz AG, Demel RA, de Kruijff S, et al. Aerobic sn-glycerol-3-phosphate from *Escherichia coli* binds to the cytoplasmic membrane through an amphipathic alpha-helix. *Biochem J*. 2002; 365:471-479.

Myerburg RJ, Castellanos A. Cardiac arrest and sudden cardiac death. In: P. ZD, Libby P, Bonow RO, et al., eds. *Braumwald's Heart disease: A textbook of cardiovascular medicine*. 7th ed. Phildadelphia: Elsevier Saunders; 2005:865-908 (Chapter 33).

Priori SG, Rivolta I, Napolitano C. Genetics of long QT, Brugada, and other channelopathies. In: P. ZD, Jalife J, eds. *Cardiac Electrophysiology: From Cell to Bedside*. 4th ed. Philadelphia: Saunders; 2004:462-470 (Chapter 50).

Sarkozy A, Brugada P. Sudden Cardiac Death and Inherited Arrhythmia Syndromes. *J Cardiovasc Electrophysiol*. 2005; 16:S8-20.

Mohler PJ, Schott JJ, Gramolini AO, et al. Ankyrin-B mutation causes type 4 long-QT cardiac arrhythmia and sudden cardiac death. *Nature*. 2003; 21:634-639.

Corrado 0, Thiene G. Arrhythmogenic right ventricular cardiomyopathy/dysplasia: clinical impact of molecular genetic studies. *Circulation*. 2006; 113:1634-1637.

Schwartz PJ, Priori SG, Dumaine R, et al. A molecular link between the sudden infant death syndrome and the long-QT syndrome. *N Engl J Med*. 2000;343:262-267.

Van Norstrand OW, Valdivia CR, Tester OJ, et al. Molecular and functional characterization of a novel GPD1-L mutations in sudden Infant Death Syndrome. Circulation 2007; 116-2253-2259.

Royer A, van Veen TA, Le Bouter S, et al. Mouse model of SCNSA-linked hereditary Lenegre's disease: age-related conduction slowing and myocardial fibrosis. *Circulation*. 2005; 111: 1738-1746.

Tan HL, Bink-Boelkens MT, Bezzina CR, et al. A sodium-channel mutation causes isolated cardiac conduction disease. *Nature*. 2001; 409:1043-1047.

Mihm MJ, Yu F, Cames CA, et al. Impaired myofibrillar energetics and oxidative injury during human atrial fibrillation. *Circulation*. 2001; 104:174-180.

Fukuda K, Davies SS, Nakajima T, et al. Oxidative mediated lipid peroxidation recapitulates proarrhythmic effects on cardiac sodium channels. *Circ Res*. 2005; 97:1262-1269.

Rubart M, Zipes DP. Mechanisms of sudden cardiac death. *J Clin Invest*. 200S; 115:2305-2315.

CAST. Preliminary report: effect of encainide and flecainide on mortality in a randomized trial of arrhythmia suppression after myocardial infarction. The Cardiac Arrhythmia Suppression Trial (CAST) Investigators. *N Engl J Med*.1989; 321:406-412.

PCT International Search Report and Written Opinion dated Jan. 30, 2009, in International App. No. PCT/US2008/011919 (12 pp.).

Krebs et al. (1999). "Na+ translocation by the NADH:ubiquinone oxidoreductase (complex I) from Klebsiella pneumoniae." Molecular Microbiology 33(2):590-598.

Udagawa et al. (1986). "Generation of Na+ electrochemical potential by the Na+-motive NADH oxidase and Na+/H+ antiport system of a moderately halophilic Vibrio costicola." J. Biol. Chem. 261(6):2616-2622.

Sanyal et al., Circulation. Oct. 16, 2007. 116(16) S185-S186, Abstract 941.

Office Action (Restriction Requirement) dated Jul. 6, 2010, in U.S. Appl. No. 12/289,005, filed Oct. 17, 2008.

Office Action dated Oct. 5, 2010, in U.S. Appl. No. 12/289,005, filed Oct. 17, 2008.

Notice of Allowance dated Jun. 23, 2011, in U.S. Appl. No. 12/289,005, filed Oct. 17, 2008.

Office Action dated Oct. 3, 2011, in co-pending U.S. Appl. No. 13/067,953, filed Jul. 11, 2011.

U.S. Appl. No. 13/067,953, filed Jul. 11, 2011.
U.S. Appl. No. 13/091,972, filed Apr. 21, 2011.
U.S. Appl. No. 11/895,883, filed Aug. 27, 2007.
U.S. Appl. No. 13/507,319, filed Jun. 21, 2012.
U.S. Appl. No. 13/585,396, filed Aug. 14, 2012.
U.S. Appl. No. 11/707,882, filed Feb. 20, 2007.
U.S. Appl. No. 13/658,943, filed Oct. 24, 2012.

Office Action dated Oct. 12, 2012, in U.S. Appl. No. 13/091,972, filed Apr. 21, 2011.

Ouzounian et al. Diastolic heart failure: mechanisms and controversies. Nature Clinical Practice Cardiovascular Medicine. 5(7):375-386, Jul. 2008.

Reed et al. FASEB Journal. The senescence-accelerated mouse: a model for the investigation of age-related oxidative stress and diastolic dysfunction. 22:Meeting Abstract Supplement, Mar. 2008, 970.39 (2 pages).

Li et al. Aging induces cardiac diastolic dysfunction, oxidative stress, accumulation of advanced glycation endproducts and protein modification. Aging Cell. 4(2):57-64, Apr. 2005.

Westermann et al. Cardiac Inflammation Contributes to Changes in the Extracellular Matrix in Patients with Heart Failure and Normal Ejection Fraction. Circulation Heart Failure. 2011;4:44-52.

Satpathy et al. Diagnosis and management of diastolic dysfunction and heart failure. American Family Physician. 73(5):841-846. Mar. 1, 2006.

Kuwahara et al. Transforming Growth Factor-β Function Blocking Prevents Myocardial Fibrosis and Diastolic Dysfunction in Pressure-Overloaded Rats. Circulation; 106:130-1352002.

Leask, Andrew. TGF-β, cardiac fibroblasts, and the fibrotic response. Cardiovascular Research. 74:207-212, Jul. 21, 2006.

Reed et al. Diastolic Dysfuntion is Associated with Cardiac Fibrosis in the Senecence-Accelerated Mouse. Circulation 120(18), Supplement 2, S762-S763, Nov. 3, 2009 (1 page).

Blom et al. Gene regulation of connective tissue growth factor: new targets for antifibrotic therapy? Matrix Biology 21 (2002) 473-482.

Kleber AG. Mechanism of Ventricular Arrhythmias: A Perspective. J. Cardiovascular Pharmacology 17(Suppl. 6):S1-S8, 1991.

Salama G et al. Deciphering Arrhythmia Mechanisms—Tools of the Trade. Card Electrophysiol Clin. Mar. 2011; 3(1):11-21 (15 pages).

Moens AL et al. Myocardial ischemia/reperfuion-injury, a clinical view on a complex pathophysiological process. International Journal of Cardiology 100 (2005) 179-190.

(56) References Cited

OTHER PUBLICATIONS

Office Action (Restriction Requirement) dated Jun. 11, 2012, in U.S. Appl. No. 12/929,786, filed Feb. 16, 2011.
Office Action dated Sep. 14, 2012, in U.S. Appl. No. 12/929,786, filed Feb. 16, 2011.
U.S. Appl. No. 12/929,786, filed Feb. 16, 2011.
Tu YX, Wernsdorfer A, Honda S, Tomita Y. Estimation of Conduction Velocity Distribution by Regularized-Least-Squares Method. IEEE Trans on Biomedical Engineering. vol. 44, No. 11, Nov. 1997: 1102-1106.
Li et al. Targeting mitochondrial reactive oxygen species as novel therapy for inflammatory diseases and cancers, Journal of Hematology & Oncology 2013, 6:19 (19 pgs).
Smith et al. Mitochondrial pharmacology, Trends in Pharmacological Sciences, Jun. 2012, vol. 33, No. 6, 341-352.
Sovari et al. Mitochondria Oxidative Stress, Connexin43 Remodeling, and Sudden Arrhythmic Death, *Circ Arrhythm Electrophysiol.* 2013;6:623-631.
Final Rejection dated Mar. 11, 2013, in U.S. Appl. No. 12/929,786, filed Feb. 16, 2011.
Office Action dated Sep. 6, 2013, in U.S. Appl. No. 13/507,319, filed Jun. 21, 2012.
Office Action dated Sep. 6, 2013, in U.S. Appl. No. 13/585,396, filed Aug. 14, 2012.
U.S. Appl. No. 14/083,841, filed Nov. 19, 2013.
Office Action dated Oct. 3, 2013, in U.S. Appl. No. 12/929,786, filed Feb. 16, 2011.
Office Action dated Nov. 5, 2013, in U.S. Appl. No. 13/507,319, filed Jun. 21, 2012.
Office Action dated Nov. 6, 2013, in U.S. Appl. No. 13/585,396, filed Aug. 14, 2012.
Sovari et al. Mitochondria-targeted antioxidant, Mito-TEMPO, prevents angiotensin II medicated connexin43 remodeling and sudden cardiac death. Journal of Investigative Medicine (Apr. 2011) vol. 59, No. 4, pp. 693-694. Abstract No. 6. Meeting Info: 2011 Combined Annual Meeting of the American Federation for Medical Research. Chicago, IL, United States. Apr. 14, 2011-Apr. 15, 2011.
Irvanian et al., The Renin-Angiotensin-Aldosterone System (RAAS) and Cardiac Arrhythmias. Heart Rhythm Jun. 2008, 5(6 Supplement 1): s12-s17.
Tomaselli et al., Oxidative stress irritates the heart. Nature Medicine. Jun. 2010, 16:648-649.
http://www.biophysics.org/2010meeting/Registration/RatesDeadlines/tabid/675/Default.aspx.
Liu et al. Mitchondrial dysfunction causing cardiac sodium channel downregulation in cardiomyopathy. *Journal of Molecular and Cellular Cardiology* 54 (2013) 25-34.
Sovari et al. (2013). Mitochondria Oxidative Stress, Connexin43 Remodeling, and Sudden Arrhythmic Death, *Circ Arrhythm Electrophysiol.* 2013;6:623-631 (with Supplemental Material (7 pgs.). Orig. published online Apr. 4, 2013.
Lotrionte et al. Review and Meta-Analysis of Incidence and Clinical Predictors of Anthracycline Cardiotoxicity. *Am J Cardiol* 2013;112:1980-1984.
Mackay et al. Assessment of Anthracycline Cardiomyopathy by Endomycardial Biopsy. Ultrastructural Pathology, 18:203-211, 1994.
Chatterjee et al. Doxorubicin Cardiomyopathy. *Cardiology* 2010;115:155-162.
De Angelis et al. Anthracycline Cardiomyopathy Is Medicated by Depletion of the Cardiac Stem Cell Pool and Is Rescued by Restoration of Progenitor Cell Function. *Circulation.* 2010;121:276-292.
Mazevet et al. Complications of chemotherapy, a basic science update. *Presse Med.* 2013; 42; e352-e361.
Octavia et al. Doxorubicin-induced cardiomyopathy: From molecular mechanisms to therapeutic strategies. *Journal of Molecular and Cellular Cardiology* 52 (2012) 1213-1225.
Chanan-Khan et al. Prevention and Management of Cardiotoxicity From Antineoplastic Therapy. *J Support Oncol.* 2004; 2:251-266.

Epstein AE, DiMarco JP, Ellenbogen KA, Estes NA, III, Freedman RA, Gettes LS, Gillinov AM, Gregoratos G, Hammill SC, Hayes DL, Hlatky MA, Newby LK, Page RL, Schoenfeld MH, Silka MJ, Stevenson LW, Sweeney MO, Tracy CM, Epstein AE, Darbar D, DiMarco JP, Dunbar SB, Estes NA, III, Ferguson TB, Jr., Hammill SC, Karasik PE, Link MS, Marine JE, Schoenfeld MH, Shanker AJ, Silka MJ, Stevenson LW, Stevenson WG, Varosy PD. 2012 ACCF/AHA/HRS focused update incorporated into the ACCF/AHA/HRS 2008 guidelines for device-based therapy of cardiac rhythm abnormalities: a report of the American College of Cardiology Foundation/American Heart Association Task Force on Practice Guidelines and the Heart Rhythm Society. *J Am Coll Cardiol* 2013;61:e6-75.
Nakahara S, Tung R, Ramirez RJ, Michowitz Y, Vaseghi M, Buch E, Gima J, Wiener I, Mahajan A, Boyle NG, Shivkumar K. Characterization of the arrhythmogenic substrate in ischemic and nonischemic cardiomyopathy implications for catheter ablation of hemodynamically unstable ventricular tachycardia. *J Am Coll Cardiol* 2010;55:2355-65.
Boriani G, Gasparini M, Lunati M, Santini M, Landolina M, Vincenti A, Curnis A, Bocchiardo M, Padeletti L, Biffi M, Allaria L, Denaro A. Characteristics of ventricular tachyarrhythmias occurring in ischemic versus nonischemic patients implanted with a biventricular cardioverter-defibrillator for primary or secondary prevention of sudden death. *Am Heart J* 2006;152:527-11.
Lindsay BD, Ambos HD, Schechtman KB, Arthur RM, Cain ME. Noninvasive detection of patients with ischemic and nonischemic heart disease prone to ventricular fibrillation. *J Am Coll Cardiol* 1990;16:1656-64.
Rouleau J, Shenasa M, de CJ, Nadeau R. Predictors of survival and sudden death in patients with stable severe congestive heart failure due to ischemic and nonischemic causes: a prospective long term study of 200 patients. *Can J Cardiol* 1990;6:453-60.
Ehlert FA, Cannom DS, Renfroe EG, Greene HL, Ledingham R, Mitchell LB, Anderson JL, Halperin BD, Herre JM, Luceri RM, Marinchak RA, Steinberg JS. Comparison of dilated cardiomyopathy and coronary artery disease in patients with life-threatening ventricular arrhythmias: Differences in presentation and outcome in the AVID registry. *Am Heart J* 2001;142:816-22.
Contractor T, Beri A, Gardiner J, Ardhanari S, Thakur R. Statins reduce appropriate implantable cardioverter-defibrillator shocks in ischemic cardiomyopathy with no benefit in nonischemic cardiomyopathy. *Am J Ther* 2012;19:413-8.
Furushima H, Chinushi M, Okamura K, Komura S, Tanabe Y, Sato A, Izumi D, Aizawa Y. Effect of dl-sotalol on mortality and recurrence of ventricular tachyarrhythmias: ischemic compared to nonischemic cardiomyopathy. *Pacing Clin Electrophysiol* 2007;30:1136-41.
Latif S, Dixit S, Callans DJ. Ventricular arrhythmias in normal hearts. *Cardiol Clin* 2008;26:367-80, vi.
Sadek MM, Marchlinski FE. Ablation of ventricular arrhythmias. *Trends Cardiovasc Med* 2014;24:296-304.
Hoffmayer KS, Gerstenfeld EP. Diagnosis and management of idiopathic ventricular tachycardia. *Curr Probl Cardiol* 2013;38:131-58.
Roberts-Thomson KC, Lau DH, Sanders P. The diagnosis and management of ventricular arrhythmias. *Nat Rev Cardiol* 2011;8:311-21.
Morin DP, Lerman BB. Management of ventricular tachycardia in the absence of structural heart disease. *Curr Treat Options Cardiovasc Med* 2007;9:356-63.
Liu M, Liu H, Jeong EM, Gu L, Dudley SC. Mitochondrial reactive oxygen species regulate the cardiac $Na^+$ channel in heart failure. *Basic Cardiovascular Sciences 2011 Scientific Sessions* 2011;Abstract:2011-A-246-AHA-BCVS.
Rutledge CA, Ng FS, Sulkin MS, Greener ID, Sergeyenko AM, Liu H, Gemel J, Beyer EC, Sovari AA, Efimov IR, Dudley SC. c-Src kinase inhibition reduces arrhythmia inducibility and connexin43 dysregulation after myocardial infarction. *J Am Coll Cardiol* 2014;63:928-34.
Davies et al. Redox Cycling of Anthracyclines by Cardiac Mitochondria, 1986, *The Journal of Biological Chemistry*, vol. 261, No. 7, 3068-3074.
World Health Organization (WHO) International Classification of Diseases (ICD) http://www.who.int/classifications/icd/en/ (2 pages) Accessed Jul. 16, 2014.

(56) References Cited

OTHER PUBLICATIONS

Cardiomyopathy (I42) and cardiomyopathy due to drug or external agent (I42.7) http://apps.who.int/classifications/icd10/browse/2010/en#/I30-I52 (1 page) Accessed Jul. 16, 2014.

Felker et al., Underlying Cause and Long-Term Survival in Patients with Initially Unexplained Cardiomyopathy. *The New England Journal of Medicine*, 2000, vol. 342, No. 15, 1077-84.

Octavia Y. et al., Doxorubicin-induced cardiomyopathy: From molecular mechanisms to therapeutic strategies. *Journal of Molecular and Cellular Cardiology*, 52, 2012, 1213-1225.

Guilherme H. et al., Increased Need for Right Ventricular Support in Patients With Chemotherapy-Induced Cardiomyopathy Undergoing Mechanical Circulatory Support. *Journal of the American College of Cardiology*, 2014, vol. 63, No. 3, 240-248.

Tabane K. et al. Cancer drugs: Highlighting the molecular mechanisms of cardiotoxicity. SA Heart, 2012;9:244-248.

Zhang S. et al., Identification of the molecular basis of doxorubicin-induced cardiotoxicity. *Nature Medicine*, 2012, vol. 18, No. 11, 1639-1642. With Online Methods (3 pgs).

Ichikawa I. et al., Cardiotoxicity of doxorubicin is mediated through mitochondrial iron accumulation. *Journal of Clinical Investigation*, 2014; vol. 124, No. 2:617-630.

Jeyaseelan R. et al., A novel Cardiac-Restricted Target for Doxorubicin. *The Journal of Biological Chemistry*, 1997, vol. 272, No. 36, 22800-22808.

Office Action dated May 14, 2014, in U.S. Appl. No. 12/929,786, filed Feb. 16, 2011.

Office Action dated Jun. 17, 2014, in U.S. Appl. No. 13/585,396, filed Aug. 14, 2012.

Office Action dated Jul. 28, 2014, in U.S. Appl. No. 13/507,319, filed Jun. 21, 2012.

\* cited by examiner

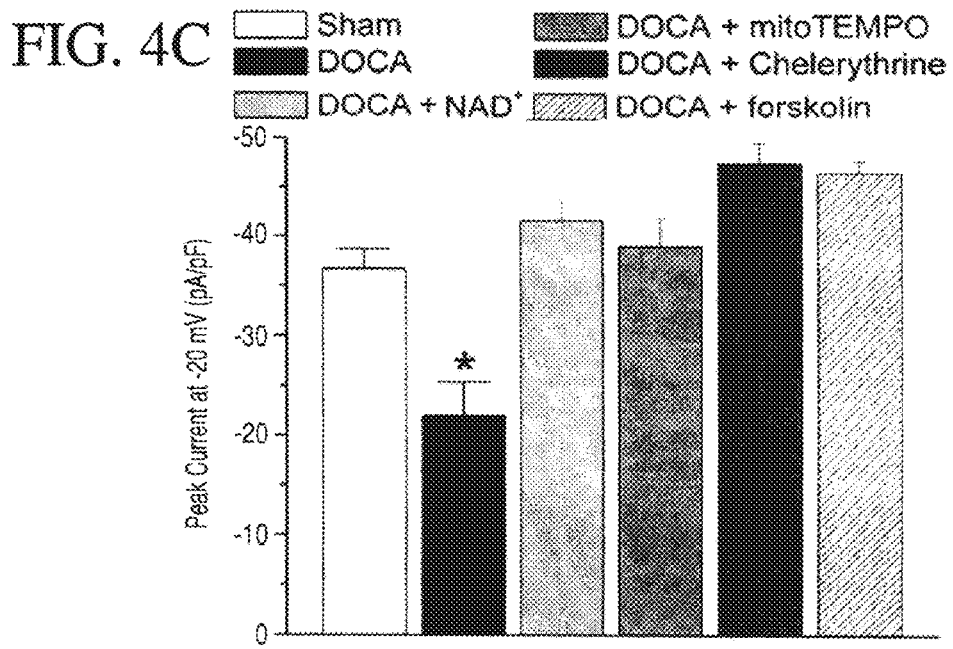
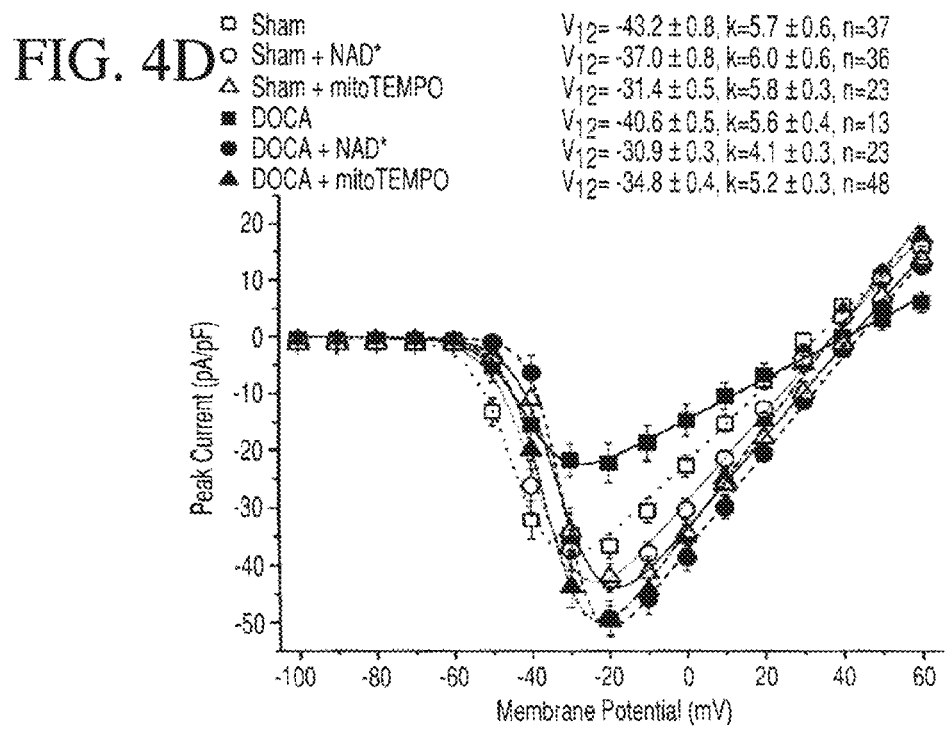

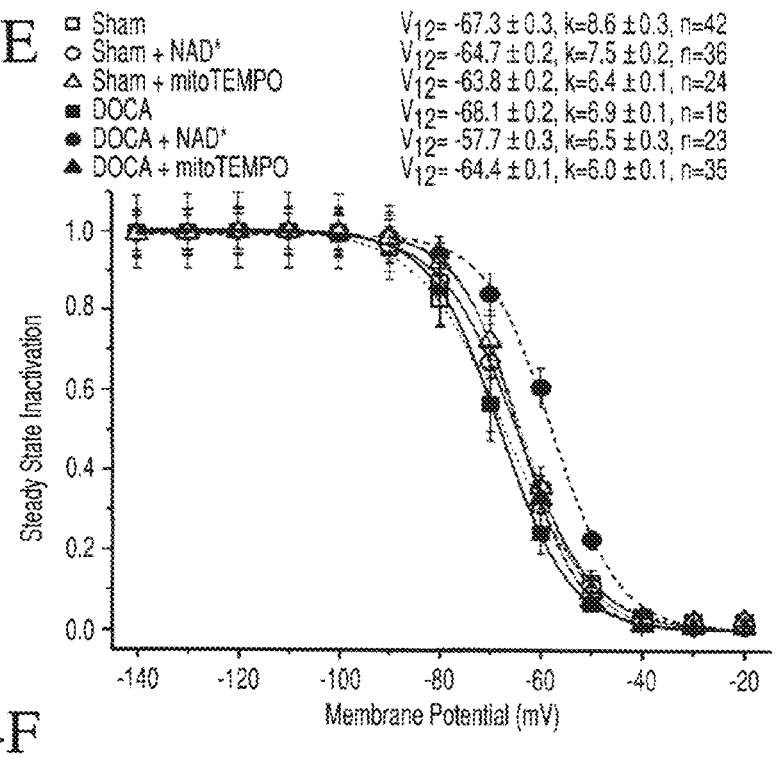
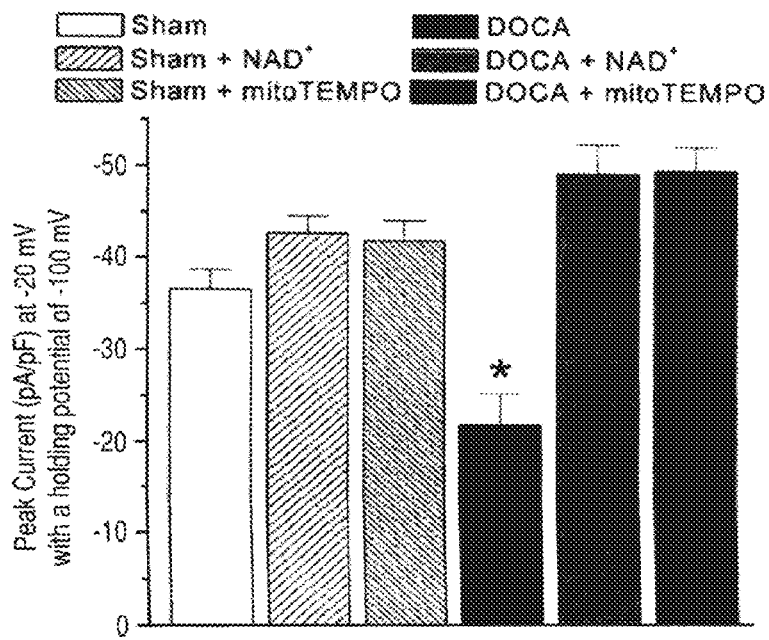

US 9,220,720 B2

METHOD FOR AMELIORATING OR PREVENTING ARRHYTHMIC RISK ASSOCIATED WITH CARDIOMYOPATHY

CROSS-REFERENCE TO RELATED APPLICATIONS

This is a continuation-in-part (CIP) application of U.S. application Ser. No. 12/929,786, filed Feb. 16, 2011, which claims the priority benefit of U.S. Provisional Patent Application Ser. No. 61/305,668, filed Feb. 18, 2010, and is a continuation-in-part (CIP) application of U.S. application Ser. No. 12/289,005, filed Oct. 17, 2008, now U.S. Pat. No. 8,003,324B2, which claims the priority benefit of U.S. Provisional Patent Application Ser. No. 60/960,883, filed Oct. 18, 2007, all of the foregoing are hereby incorporated herein in their entirety by reference.

STATEMENT REGARDING FEDERALLY SPONSORED RESEARCH OR DEVELOPMENT

The invention was made with government supported under grants NIH R01 HL085558, R01 HL072742, R01 HL106592, R01 HL104025, T32 HL072742, and P01 HL058000 (SCD), and a VA MERIT grant. The government has certain rights in the invention.

FIELD AND BACKGROUND OF THE INVENTION

The present invention is generally directed to cardiac therapy, and more particularly to ameliorating, preventing, and/or reversing arrhythmic risk associated with cardiomyopathy.

Despite extensive research and novel treatments, conditions associated with deranged cardiac metabolism, such as heart failure or ischemia, are still accompanied by a substantial risk of arrhythmic sudden death (Reference 1). While implanted cardiac defibrillators have decreased sudden death risk, they can cause physical and psychological complications. They are also expensive, and do not address the underlying pathology that leads to arrhythmic risk (References 2-3). A more complete molecular understanding of the basis for the increased arrhythmic risk is likely to lead to new therapies that will be more effective and less invasive.

Cardiac injury from many causes is associated with altered metabolism and downregulation of the cardiac $Na^+$ channel ($Na_v 1.5$) (References 4-7). Recently, we reported that an elevation of intracellular reduced nicotinamide adenine dinucleotide (NADH) can downregulate $Na^+$ current ($I_{Na}$) acutely and to a degree that is large enough to be clinically significant (Reference 8). The signaling cascade involves a protein kinase C (PKC)-mediated increase in mitochondrial reactive oxygen species (ROS) production (References 9-10). NADH is known to oscillate with myocardial ischemia, and mitochondrial injury is associated with increased NADH and ROS levels (References 11-12). These changes could contribute to reduced $I_{Na}$, conduction block, and arrhythmic risk known to exist with reduced cardiac contractility. The NADH effect on ROS production and $I_{Na}$ can be antagonized by PKA activation mediated by $NAD^+$, by superoxide dismutase, or by 2-(2,2,6,6-Tetramethylpiperidin-1-oxyl-4-ylamino)-2-oxoethyl)triphenylphosphonium chloride (MitoTEMPO), a scavenger of mitochondrial ROS (References 9-10).

In this study, we tested whether NADH and mitochondrial ROS were elevated in nonischemic cardiomyopathy and whether these changes resulted in a reduction in $I_{Na}$. We also investigated whether $NAD^+$ and 2-(2,2,6,6-Tetramethylpiperidin-1-oxyl-4-ylamino)-2-oxoethyl)triphenylphosphonium chloride (MitoTEMPO) could counteract the effects of NADH on mitochondrial ROS and cardiac $I_{Na}$ in nonischemic cardiomyopathy. The PKC inhibitor chelerythrine and PKA activator forskolin were utilized to test whether they participated in the signaling pathway of $NADH/NAD^+$ modification of the $Na_v 1.5$ of DOCA myocytes.

ASPECTS OF THE INVENTION

The present disclosure is directed to various aspects of the present invention.

One aspect of the present invention includes discovery and/or demonstration that mitochondria are the main source of NADH-dependent ROS downregulating sodium channel current ($I_{Na}$) in cardiomyopathic cells.

Another aspect of the present invention includes discovery and/or demonstration that mitochondrial superoxide release is responsible for downregulation of $I_{Na}$ in cardiomyopathic cells.

Another aspect of the present invention includes discovery and/or demonstration that elevation in intracellular NADH results in activation of protein kinase C (PKE) and subsequent mitochondrial complex III release of reactive oxygen species (ROS) through the mitochondrial inner member anion channel (IMAC) in cardiomyopathic cells.

Another aspect of the present invention includes discovery and/or demonstration that inhibition of mitochondrial ROS overproduction by one or more strategies prevents or suppresses $I_{Na}$ downregulation by NADH in cardiomyopathic cells.

Another aspect of the present invention includes suggestions and/or development of possible therapeutic approaches or strategies to reduce or prevent arrhythmic risk associated with cardiomyopathy.

Another aspect of the present invention includes a method for reducing arrhythmic risk associated with cardiomyopathy, including the step of administering a composition containing $NAD^+$ to an individual in need thereof.

Another aspect of the present invention includes a method for restoring the cardiac sodium current to a normal level in an individual with cardiomyopathy, including the step of administering a composition containing $NAD^+$ to an individual in need thereof.

Another aspect of the present invention includes a method for reducing arrhythmic risk in an individual with cardiomyopathy and a cardiac ejection fraction of less than 50%, including the step of administering a composition containing $NAD^+$ to an individual in need thereof.

Another aspect of the present invention includes a method for reducing arrhythmic risk associated with cardiomyopathy, including the step of administering a mitochondrial targeted antioxidant to an individual in need thereof.

Another aspect of the present invention includes a method for restoring the cardiac sodium current to a normal level in an individual with cardiomyopathy, including the step of administering a mitochondrial targeted antioxidant to an individual in need thereof.

Another aspect of the present invention includes a method for reducing arrhythmic risk in an individual with cardiomyopathy and a cardiac ejection fraction of less than 50%, including the step of administering a mitochondrial targeted antioxidant to an individual in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

One of the above and other aspects, novel features and advantages of the present invention will become apparent from the following detailed description of the non-limiting preferred embodiment(s) of invention, illustrated in the accompanying drawings, wherein:

FIG. 2A illustrates representative whole cell current traces of $I_{Na}$ from sham and DOCA mouse ventricular cardiomyocytes held at −100 mV and measured from −100 to +60 mV with 10 mV steps;

FIG. 2B illustrates peak $I_{Na}$ from sham and DOCA mice ventricular cardiomyocytes measured at −20 mV. *P<0.01;

FIGS. 4A-F illustrate that reduced $I_{Na}$ in cardiomyopathy was corrected by NAD$^+$ or 2-(2,2,6,6-Tetramethylpiperidin-1-oxyl-4-ylamino)-2-oxoethyl)triphenylphosphonium chloride (MitoTEMPO) without significant changes in channel gating;

FIG. 4A illustrates the peak current-voltage relationship;

FIG. 4B illustrates the voltage dependence of steady state inactivation of isolated cardiomyocytes from sham and DOCA mouse model treated with NAD$^+$, 2-(2,2,6,6-Tetramethylpiperidin-1-oxyl-4-ylamino)-2-oxoethyl)triphenylphosphonium chloride (MitoTEMPO), chelerythrine, or forskolin. The minor shifts of V$_{1/2}$ values of steady state gating were not enough to affect the evaluation of the peak currents;

FIG. 4C illustrates application of NAD$^+$, 2-(2,2,6,6-Tetramethylpiperidin-1-oxyl-4-ylamino)-2-oxoethyl)triphenylphosphonium chloride (MitoTEMPO), chelerythrine, or forskolin (500, 10, 50, or 5 μM, respectively) intracellularly to isolated cardiomyocytes of DOCA mouse model restored the decreased peak $I_{Na}$ in cardiomyopathic DOCA myocytes at −20 mV. *P<0.01 vs sham group;

FIG. 4D illustrates the peak current-voltage relationship of isolated cardiomyocytes from sham and DOCA mouse model with injection of NAD$^+$ or 2-(2,2,6,6-Tetramethylpiperidin-1-oxyl-4-ylamino)-2-oxoethyl)triphenylphosphonium chloride (MitoTEMPO) (100 or 0.7 mg/kg, respectively). The minor shifts of V$_{1/2}$ values of steady state gating were not enough to affect the evaluation of the peak currents;

FIG. 4E illustrates the voltage dependence of steady state inactivation of isolated cardiomyocytes from sham and DOCA mouse model with injection of NAD$^+$ or 2-(2,2,6,6-Tetramethylpiperidin-1-oxyl-4-ylamino)-2-oxoethyl)triphenylphosphonium chloride (MitoTEMPO) (100 or 0.7 mg/kg, respectively). The minor shifts of V$_{1/2}$ values of steady state gating were not enough to affect the evaluation of the peak currents;

FIG. 4F illustrates DOCA mice injected with NAD$^+$ or 2-(2,2,6,6-Tetramethylpiperidin-1-oxyl-4-ylamino)-2-oxoethyl)triphenylphosphonium chloride (MitoTEMPO) (100 or 0.7 mg/kg, respectively) showed recovered $I_{Na}$. *P<0.01 vs sham group;

FIG. 5A illustrates mitochondrial ROS overproduction was observed with DOCA mice myocytes by MitoSOX™ Red (2.9±0.3-fold of sham, P<0.01). DOCA cardiomyocyte treatment with NAD$^+$, 2-(2,2,6,6-Tetramethylpiperidin-1-oxyl-4-ylamino)-2-oxoethyl)triphenylphosphonium chloride (MitoTEMPO), δV1-1, or forskolin (500, 10, 50, or 5 μmol/L, respectively) extracellularly decreased ROS levels in myopathic mouse myocytes similar to the sham group (1.4±0.1, 1.1±0.1, 0.9±0.1, or 0.8±0.1-fold of sham, respectively, P>0.05). Three to five animals were tested in each group, and total 29-43 cells were used for average;

FIG. 5B illustrates DOCA mice injected with NAD$^+$ (100 mg/kg) or 2-(2,2,6,6-Tetramethylpiperidin-1-oxyl-4-ylamino)-2-oxoethyl)triphenylphosphonium chloride (MitoTEMPO) (0.7 mg/kg) had decreased mitochondrial ROS (1.1±0.1- or 1.1±0.2-fold of sham, respectively, P>0.05). Three to four animals were tested in each group; and FIG. 5C illustrates representative images from confocal microscopy obtained before and after treatment of myocytes in vitro, labeled with MitoTracker™ Green and MitoSOX™ Red. The white scale bar is 20 μm.

DETAILED DESCRIPTION OF THE PREFERRED EMBODIMENT(S) OF THE INVENTION

Figure 1:
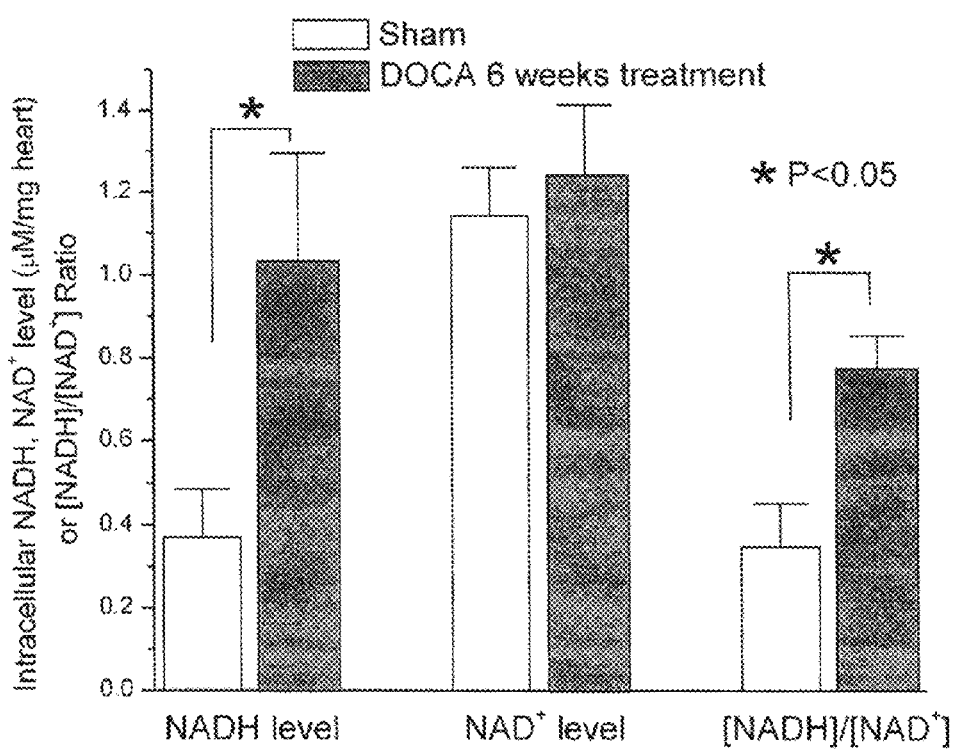
FIG. 1 illustrates intracellular NADH and NAD$^+$ levels and the [NADH]$_i$/[NAD$^+$]$_i$ ratio measured in sham and DOCA cardiomyopathic heart tissue. Increased NADH level and [NADH]$_i$/[NAD$^+$]$_i$ ratio were seen in DOCA mice.

Cardiomyopathy is associated with cardiac Na$^+$ channel downregulation that may contribute to arrhythmias. Previously, we have shown that elevated intracellular NADH causes a decrease in cardiac Na$^+$ current ($I_{Na}$) signaled by an increase in mitochondrial reactive oxygen species (ROS). The decrease in $I_N$, can be ameliorated by NAD$^+$ or a mitochondrial specific antioxidant, 2-(2,2,6,6-Tetramethylpiperidin-1-oxyl-4-ylamino)-2-oxoethyl)triphenylphosphonium chloride (MitoTEMPO).

Here, we tested whether the NADH-mitochondrial ROS pathway was involved in the reduction in $I_{Na}$ in a nonischemic cardiomyopathic model.

Materials and Methods

Model Generation and Isolation of Mice Ventricular Myocytes

Nonischemic cardiomyopathy was induced in C57BL/6 mice by six weeks of hypertension evoked after unilateral nephrectomy, deoxycorticosterone acetate (DOCA) pellet implantation, and 1% salt water substitution (Reference 13). Sham operated mice were used as controls. Ketamine (100 mg/kg) and xylazine (10 mg/kg) were administrated by IP pre-operation and buprenorphine (0.1 mg/kg) was injected subcutaneously post-operation and at 12-hour interval as needed. For each experiment, three to eight mice were used.

Ventricular myocytes were isolated as described before (References 13-14). Briefly, hearts were excised from anesthetized mice, perfused with perfusion buffer (in mmol/L: NaCl 113, KCl 4.7, Na$_2$HPO$_4$ 0.6, KH$_2$PO$_4$ 0.6, MgSO$_4$ 1.2, Phenol Red 0.032, NaHCO$_3$ 12, KHCO$_3$ 10, HEPES 10, Taurine 30, 2-3-butanedione monoxime 10) and digested with collagenase II (Worthington Biochemical Co. Lakewood, N.J.). Cardiomyocytes were washed with control buffers (in mmol/L: NaCl 133.5, KCl 4, Na$_2$HPO$_4$ 1.2, HEPES 10, MgSO$_4$ 1.2) with serially increasing Ca$^{2+}$ concentrations (0.2, 0.5, and 1 mmol/L). Then, myocytes were incubated in MEM medium (modified Eagle's medium with 1% insulin-transferrin-selenium, 0.1% bovine serum albumin, 1% glucose, and 1% penicillin/streptomycin) in a 95% $O_2$/5% $CO_2$ incubator at 37° C. for 2 hours prior to being used for patch clamp recording and ROS level measurements.

Documentation of Cardiomyopathy

Blood pressure and heart rate were measured on acclimated conscious mice six weeks after surgery using tail-cuff plethysmography (Columbus Instruments, Columbus, Ohio). Transthoracic echocardiography was performed using the Vevo 770 system equipped with a RMV-707B transducer (VisualSonics, Toronto, Canada). Mice were anesthetized with 1% isoflurane in oxygen and were closely monitored during the procedure. Images were obtained from the parasternal long axis view and parasternal short axis view at the midpapillary level. Wall thickness, chamber size, fractional shortening (% FS), and ejection fraction (% EF) were evaluated by two-dimensional and M-mode echocardiography. Measurements were averaged from three consecutive beats.

Intracellular NADH and $NAD^+$ Levels

Intracellular NADH and $NAD^+$ levels ($[NADH]_i$ and $[NAD^+]_i$) were detected using the EnzyChrom™ $NAD^+$/NADH Assay Kit (BioAssay Systems, Hayward, Calif.) with sham and DOCA mice heart tissue followed the manufacturer's instructions. The intensity difference of the reduced product color, measured at 565 nm at time zero and 15 min later, was proportional to the change in the concentration of NAD(H).

Cellular Electrophysiology $Na^+$ currents were measured using the whole-cell patch clamp technique in voltage-clamp mode at room temperature (References 9-10). To measure $Na^+$ currents, pipettes (1-2 MΩ) were filled with a pipette solution containing (in mmol/L): CsCl 80, cesium aspartate 80, EGTA 11, $MgCl_2$ 1, $CaCl_2$ 1, HEPES 10, and $Na_2ATP$ 5 (adjusted to pH 7.4 with CsOH). The bath solution consisted of (in mmol/L): NaCl 15, CsCl 5, $CaCl_2$ 1, $MgCl_2$ 1, tetramethylammonium Cl 20, N-methyl-D-glucamine 100, 4-aminopyride 3, $MnCl_2$ 2, HEPES 10 and glucose 10 (adjusted to pH 7.4 with CsOH). A stepped voltage protocol from −100 to +60 mV with a holding potential of −100 mV was applied to establish the presence of $Na_v$ 1.5. Peak currents obtained during steps to −20 mV were used for comparison in determining the relative reduction of $I_{Na}$. To minimize time-dependent drift in gating parameters, all protocols were initiated 2-5 min after whole-cell configuration was obtained. The currents were normalized with cell capacitance.

Measurement of Mitochondrial ROS

To measure mitochondrial ROS, the fluorescent probe MitoSOX™ Red was used according to the manufacturer's protocol. Briefly, eight groups of isolated cardiomyocytes were studied: sham mouse myocytes, DOCA mouse myocytes, myocytes from sham or DOCA mice treated with 500 µmol/L $NAD^+$, 10 µmol/L 2-(2,2,6,6-Tetramethylpiperidin-1-oxyl-4-ylamino)-2-oxoethyl)triphenylphosphonium chloride (MitoTEMPO), 50 µmol/L chelerythrine, or 5 µmol/L forskolin for 10 min at room temperature, and myocytes from sham or DOCA mice injected with 100 mg/kg $NAD^+$ or with 0.7 mg/kg 2-(2,2,6,6-Tetramethylpiperidin-1-oxyl-4-ylamino)-2-oxoethyl)triphenylphosphonium chloride (MitoTEMPO) twice (at 24 h and 1 h before myocyte isolation, respectively). Cells were incubated with 5 µmol/L MitoSOX™ Red and 100 nmol/L MitoTracker Green for 10 min at 37° C., followed by washing three times with MEM medium. Images were taken on a Zeiss LSM710 confocal microscope (Carl Zeiss GmbH, Oberkochen, Germany) using an argon laser excitation (514 nm) with emission collection through a 560 nm long pass filter. The mean values of the whole cell fluorescence of MitoSOX™ Red were obtained with ImageJ software.

For flow cytometry measurements, isolated cardiomyocytes from sham or DOCA with/without treatments were incubated with MitoSOX™ Red (5 µmol/L) for 15 min and washed twice with media. Appropriate gating was used to select cardiomyocytes, and ~10,000 cells were read in each sample at FL-2 in CyAN ADP flow cytometry (Beckman-Coulter, Brea, Calif.).

Biotinylation and Western Blotting of $Na_v$ 1.5

Biotinylation with the Pierce® Cell Surface Protein Isolation Kit (Pierce Biotechnology, Rockford, Ill.) and analysis $Na^+$ channels present at the cell surface were performed on freshly isolated cardiomyocytes of sham and DOCA mice as previously described (Reference 15). For detection of $Na_v$ 1.5, the primary antibody (rabbit anti-SCN5A, Alomone Labs, Jerusalem, Israel) was diluted 1:200. Horseradish peroxidase-conjugated goat anti-rabbit IgG secondary antibody (Cell Signaling Technology, Danvers, Mass.) was diluted 1:5000. Actin (Santa Cruz Biotechnology, CA) was used as a loading control.

SCN5A RNA Abundance

Total RNA was isolated (RNeasy Minikit—Qiagen, Valencia, Calif.) from snap frozen ventricular tissue samples taken from sham and DOCA mice (n=3 per group). Equal quantities of total RNA from all samples were used to generate cDNA using the High Capacity cDNA synthesis kit (Applied Biosystems, Carlsbad, Calif.), and quantitative PCR was performed using Fast SYBR green chemistry (Applied Biosystems, Carlsbad, Calif.) on an ABI 7500 platform. Primers were designed against mouse SCN5A (SCN5A_F TTGCTC-CTTCTCTCATGGTTG and SCN5A_R CATGGAGAT-GCTCAAGAAGGA) and Hypoxanthine phosphoribosyl-transferase (HPRT) (HPRT_F AGGCCAGACTTTGTTGGATTT and HPRT_R GGCTTTGTATTTGGCTTTTCC) using Primer3 plus software (http://www.bioinformatics.nl/cgi-bin/primer3plus) and synthesized by MWG (Huntsville, Ala.). HPRT acted as the housekeeping gene by which to normalize SCN5A cDNA. The $2^{-\Delta\Delta Ct}$ method was used for relative quantification between groups. A t-test was used for test for statistical comparison between the two groups.

Statistical Evaluations

Data are shown as the mean±SEM. Aside from above, determinations of statistical significance were performed with ANOVA with the Bonferroni correction for comparisons of multiple means. A value of P<0.05 was considered statistically significant.

Results

At 6 weeks after surgery, DOCA mice had developed hypertension by tail-cuff blood pressure measurements and systolic heart dysfunction by echocardiography (Table 1). Compared to the sham mice, DOCA mice showed higher artery blood pressure, enlarged left ventricular chamber, and reduced ejection fraction (P<0.05).

TABLE 1

Blood pressure and Echocardiographic Comparison Between DOCA and Sham Mice

|  | Sham | | DOCA | | |
| --- | --- | --- | --- | --- | --- |
|  | Value | N | Value | N | P value |
| Heart rate (bpm) | 528 ± 17 | 4 | 533 ± 28 | 5 | NS |
| SBP (mmHg) | 99 ± 7 | 4 | 116 ± 3 | 5 | <0.05 |
| DBP (mmHg) | 74 ± 5 | 4 | 89 ± 3 | 5 | <0.05 |
| LVESV (µL) | 42.1 ± 3.6 | 8 | 64.6 ± 3.3 | 8 | <0.05 |
| LVEDV (µL) | 87.9 ± 6.1 | 8 | 104.7 ± 3.9 | 8 | <0.05 |

TABLE 1-continued

Blood pressure and Echocardiographic
Comparison Between DOCA and Sham Mice

|  | Sham | | DOCA | | |
| --- | --- | --- | --- | --- | --- |
|  | Value | N | Value | N | P value |
| FS (%) | 26.4 ± 1.0 | 8 | 17.9 ± 1.0 | 8 | <0.05 |
| EF (%) | 49.4 ± 3.7 | 8 | 37.1 ± 1.8 | 8 | <0.05 |

Note:
SBP: systolic artery blood pressure;
DBP: diastolic artery blood pressure;
LVESV: left ventricular end-systolic volume;
LVEDV: left ventricular end-diastolic volume;
FS: fractional shortening;
EF: ejection fraction.
Values were compared between DOCA and sham mice at 6 weeks post surgery.
N is the animal number used.

Elevated NADH Level in Cardiomyopathic Heart Tissue

We measured [NADH]$_i$ and [NAD$^+$]$_i$ in heart tissue of sham and DOCA mice. FIG. 1 shows that the [NAD$^+$]$_i$ of sham and DOCA groups were similar. On the other hand, [NADH]$_i$ was increased 2.8±0.7-fold in DOCA mice (P<0.01 vs. sham). According to our previous work, this amount of increase in intracellular NADH level could lead to significant decrease of I$_{Na}$ (Reference 9). Therefore, we measured the I$_{Na}$ of isolated myocytes of sham and DOCA mice.

Decreased I$_{Na}$ in Cardiomyopathic Ventricular Cardiomyocytes

Figures 2A, 2B:
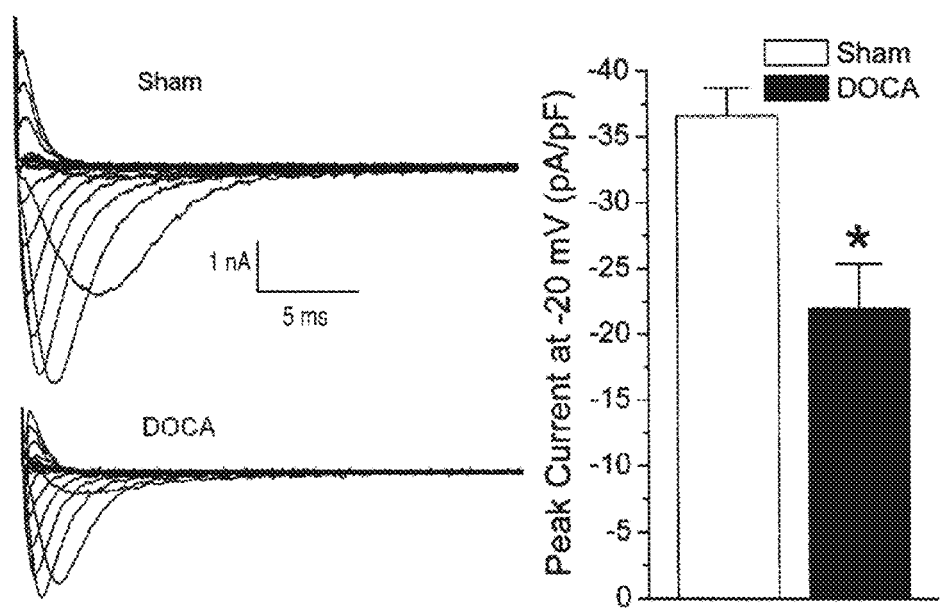
FIGS. 2A-B illustrate that decreased $I_{Na}$ was seen in DOCA cardiomyopathic mice.
Figure 3:
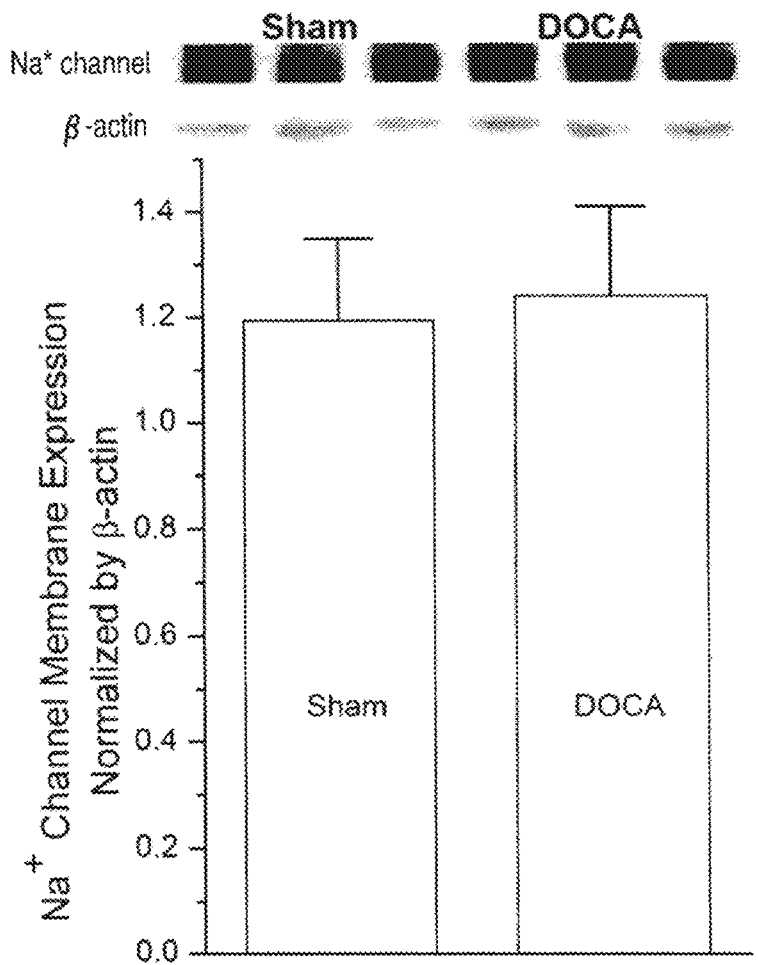
FIG. 3 illustrates Na$_v$ 1.5 membrane expression measured with biotinylation as unchanged between sham and DOCA mice. In these Western blots, β-actin was used as a loading control. There is no significant change of Na$_v$ 1.5 protein membrane expressions in DOCA mice cardiomyocytes.

FIG. 2A shows representative traces of I$_{Na}$ measured from isolated sham and DOCA ventricular myocytes. I$_{Na}$ of DOCA myocytes was significantly decreased. FIG. 2B presents the averaged peak currents measured at −20 mV with a holding potential of −100 mV. I$_{Na}$ of the cardiomyopathy group was 59±8% of the sham (P<0.01). The decrease in I$_{Na}$ was not related to changes in transcription. Quantification of cardiac sodium channel (SCN5A) mRNA revealed no significant difference in transcript levels between the two groups (P=0.95). To investigate the Na$_v$ 1.5 membrane expression, we marked channels present at the membrane surface with biotinylation. Western blot analysis for biotinylated Na$^+$ channels showed no significant difference between sham and DOCA mice (FIG. 3: 1.19±0.16 vs. 1.24±0.17, n=3 for each group, P=0.90).

Restoring I$_{Na}$ with Treatment

Figure 4A:
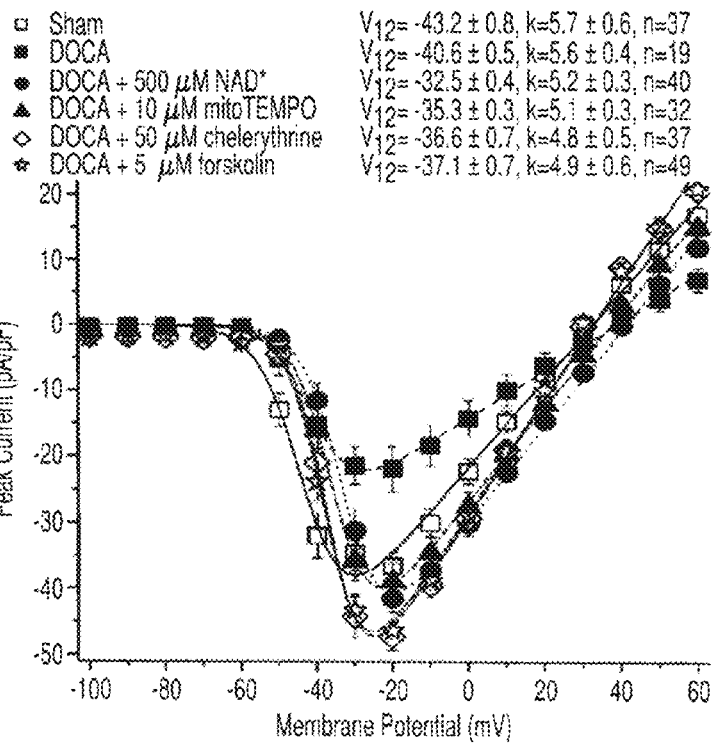
Figure 4B:
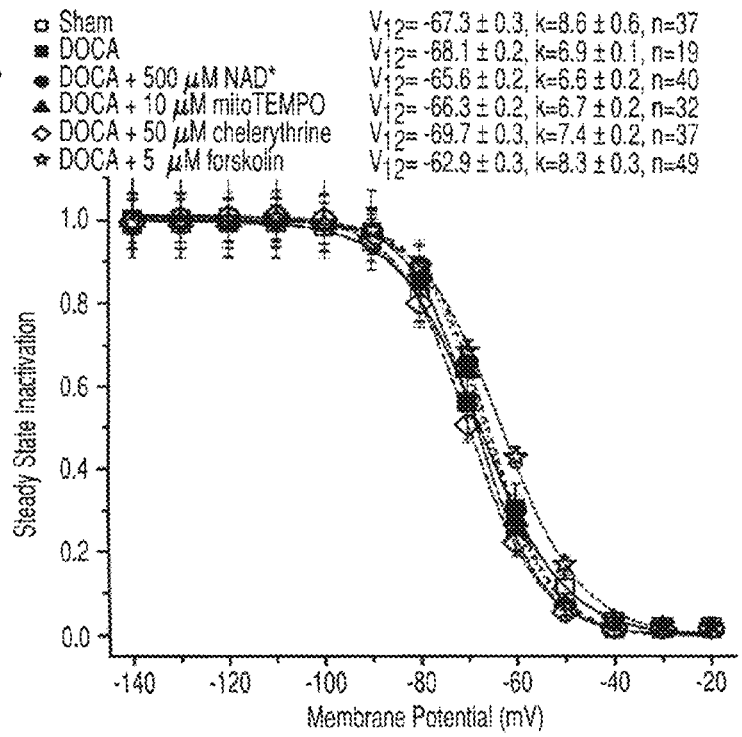

In our previous studies, NAD$^+$ and 2-(2,2,6,6-Tetramethylpiperidin-1-oxyl-4-ylamino)-2-oxoethyl)triphenylphosphonium chloride (MitoTEMPO) reversed the NADH-induced decrease of I$_{Na}$ by decreasing mitochondrial ROS production (References 9-10). Applied to isolated myocytes, NAD$^+$, 2-(2,2,6,6-Tetramethylpiperidin-1-oxyl-4-ylamino)-2-oxoethyl)triphenylphosphonium chloride (MitoTEMPO), chelerythrine, or forskolin (500, 10, 50, or 5 µmol/L, respectively) increased I$_{Na}$ to 113±5%, 106±8%, 129±6%, 126±3% of sham at −20 mV, respectively (FIGS. 4A and 4C, P>0.05). As shown in FIGS. 4A and 4B, there were minor shifts of V$_{1/2}$ values of steady state activation and inactivation, but they were not enough to affect the evaluation of the peak currents. Treatment of sham myocytes with these compounds had no effect on I$_{Na}$.

Treating animals with NAD$^+$ and 2-(2,2,6,6-Tetramethylpiperidin-1-oxyl-4-ylamino)-2-oxoethyl)triphenylphosphonium chloride (MitoTEMPO) had similar effects as applying these compounds to isolated myocytes. We injected the animals twice with NAD$^+$ (100 mg/kg) or 2-(2,2,6,6-Tetramethylpiperidin-1-oxyl-4-ylamino)-2-oxoethyl)triphenylphosphonium chloride (MitoTEMPO) (0.7 mg/kg), at 24 hours and 1 hour before the myocyte isolation. As shown in FIGS. 4D and 4F, NAD$^+$ or 2-(2,2,6,6-Tetramethylpiperidin-1-oxyl-4-ylamino)-2-oxoethyl)triphenylphosphonium chloride (MitoTEMPO) completely restored the decreased I$_{Na}$ seen in myopathic myocytes (113±5% and 106±8% of sham injected with NAD$^+$ or 2-(2,2,6,6-Tetramethylpiperidin-1-oxyl-4-ylamino)-2-oxoethyl)triphenylphosphonium chloride (MitoTEMPO), respectively, at −20 mV, P>0.05). As shown in FIGS. 4D and 4E, there were also minor shifts of V$_{1/2}$ values of steady state activation and inactivation that were not enough to affect the evaluation of the peak currents.

Mitochondrial ROS are Increased in Myopathic Ventricular Myocytes

Figure 5A:
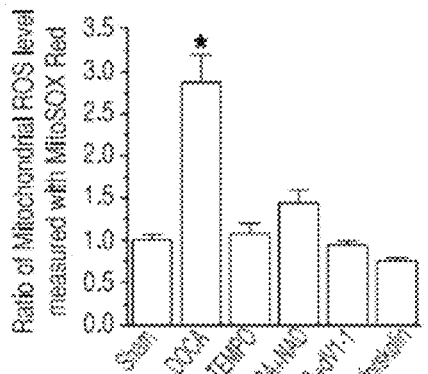
FIGS. 5A-C illustrate that mitochondrial ROS levels were increased in DOCA myopathic mice and reduced by NAD$^+$, 2-(2,2,6,6-Tetramethylpiperidin-1-oxyl-4-ylamino)-2-oxoethyl)triphenylphosphonium chloride (MitoTEMPO), δV1-1 and forskolin.

Previously, we have shown that elevated NADH increases mitochondrial ROS production causing a reduction of Na$^+$ current (References 9-10). To test if this mechanism of the I$_{Na}$ reduction was similar in a clinically relevant model, Mito-SOX™ Red was used to demonstrate mitochondrial ROS production in myopathic ventricular myocytes of DOCA mice. As shown in FIG. 5A, the mitochondrial ROS level of myopathic myocytes increased ~2.9±0.3-fold (P<0.01 vs. sham). This is similar to a four-fold increase of superoxide production observed in the aortas of DOCA mice (Reference 16).

Figure 5B:
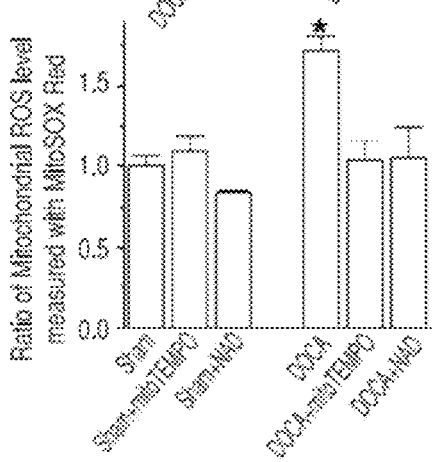
Figure 5C:
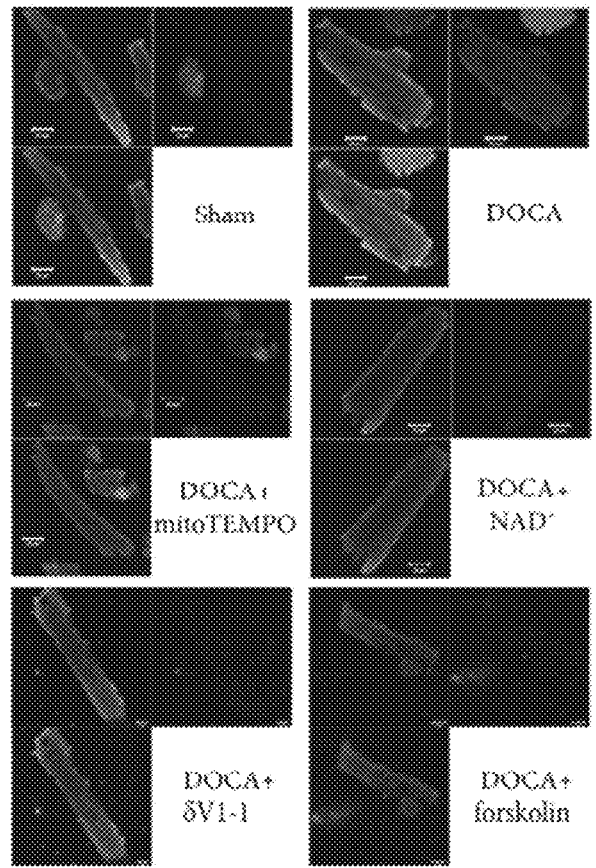

Treatment of cells with NAD$^+$, 2-(2,2,6,6-Tetramethylpiperidin-1-oxyl-4-ylamino)-2-oxoethyl)triphenylphosphonium chloride (MitoTEMPO), δV1-1, or forskolin (500, 10, 50, or 5 µmol/L, respectively) extracellularly led to decrease of ROS in myopathic mouse myocytes to the level similar to the sham group (1.4±0.1, 1.1±0.1, 0.9±0.1, or 0.8±0.1-fold of sham, respectively, P>0.05). Here we used the specific inhibitor δV1-1 of PKC instead of chelerythrine, because chelerythrine was yellow and affected the calculation of Mito-SOX™ Red fluorescence. FIG. 5C shows representative confocal images of these measurements. Treatment of sham myocytes with NAD$^+$ and 2-(2,2,6,6-Tetramethylpiperidin-1-oxyl-4-ylamino)-2-oxoethyl)triphenylphosphonium chloride (MitoTEMPO) had no effect on mitochondrial ROS production (data not shown). Similar results were obtained with injection of NAD$^+$ or 2-(2,2,6,6-Tetramethylpiperidin-1-oxyl-4-ylamino)-2-oxoethyl)triphenylphosphonium chloride (MitoTEMPO) into DOCA mice (100 mg/kg or 0.7 mg/kg, respectively; FIG. 5B). The mean fluorescent intensity of the myopathic group was increased by 1.7±0.1-fold when compared to sham (P<0.05). NAD$^+$ and 2-(2,2,6,6-Tetramethylpiperidin-1-oxyl-4-ylamino)-2-oxoethyl)triphenylphosphonium chloride (MitoTEMPO) decreased the mitochondrial ROS overproduction in myopathic mouse myocytes to 1.1±0.2-fold and 1.0±0.1-fold of sham, respectively (P>0.05).

Discussion

Voltage-gated Na$^+$ channels are responsible for generating the main current for excitation propagation in the membrane of most excitable cells, such as cardiomyocytes and neurons (References 17-19). Cardiac Na$^+$ channel changes have been implicated in the increased risk of sudden death in heart failure (References 20-22). These changes appear to happen in the absence of significant alterations in the β-subunits of Na$^+$ channel, suggesting an issue involving the α-subunit (References 4 and 23). In our previous studies on the mechanism by which mutations in glycerol-3-phosphate dehydrogenase 1 like (GPD1L) protein cause reduced I$_{Na}$ and Brugada Syndrome, we have shown that increased NADH can downregulate the cardiac Na$^+$ channel through PKC activation and mitochondrial ROS overproduction (References 9-10). Here, we evaluated whether the metabolic derangements occurring in cardiomyopathy could result in reductions in $I_{Na}$ by a similar mechanism.

In this study, hypertensive mice presented with nonischemic cardiomyopathy associated with elevated intracellular NADH, increased mitochondrial ROS, and reduced $I_{Na}$. The reduction in $I_{Na}$ was on the order of that seen in Brugada Syndrome, and was not the result of changes in SCN5A RNA abundance or $Na_v 1.5$ protein membrane expression. The reasons could be decreases of the probability of channel opening or of the single channel conductance. Further studies will be needed to differentiate these two mechanisms. The increase in mitochondrial ROS is consistent with other studies showing DOCA-salt treatment increases ROS production. Elevated oxidative stress has also been observed in the aorta of DOCA hypertension rat (References 24-25) and mice (Reference 16). Previously, we have reported this model increases cardiac oxidation (Reference 13).

Similar findings were seen in cardiomyocytes overexpressing a GPD1L mutant A280V associated with Brugada Syndrome (Reference 9). In those studies, we have demonstrated that an elevated NADH level leads to PKC activation and ROS overproduction from the mitochondrial electron transport chain (ETC) (Reference 10). In the case of the GPD1L mutant, $NAD^+$ and 2-(2,2,6,6-Tetramethylpiperidin-1-oxyl-4-ylamino)-2-oxoethyl)triphenylphosphonium chloride (MitoTEMPO) were able to reverse the phenotype and reduce spontaneously induced arrhythmias in a mouse model of Brugada Syndrome. In this study, we found that these compounds had analogous effects to raise $I_{Na}$ in a nonischemic cardiomyopathy model. Treating either myocytes directly or the animal, $NAD^+$ and 2-(2,2,6,6-Tetramethylpiperidin-1-oxyl-4-ylamino)-2-oxoethyl)triphenylphosphonium chloride (MitoTEMPO) were able to reduce mitochondrial ROS production and increase $I_{Na}$. This suggests that while there may be other sources of oxidative stress in nonischemic cardiomyopathy, mitochondrial ROS are most important for a reduction in $I_{Na}$. Interestingly, 2-(2,2,6,6-Tetramethylpiperidin-1-oxyl-4-ylamino)-2-oxoethyl)triphenylphosphonium chloride (MitoTEMPO) has also been tested in 10-day DOCA mice that showed hypertension, and reduced blood pressure has been observed (Reference 26).

We also examined the PKA activator forskolin and PKC inhibitors chelerythrine and δV1-1. They enhanced the $I_{Na}$ and blunted the elevated mitochondrial ROS level of DOCA mice myocytes to the levels of sham mice.

This indicates that, similar to the mechanism we have found in the mutant A280V GDP1L modulation of the cardiac $Na_v 1.5$ (References 9-10), PKC activation participates in the signaling pathway of decreasing the $I_{Na}$ in DOCA mice, and that PKA activation is likely involved in $NAD^+$ upregulation of the cardiac $Na_v 1.5$ of DOCA mice myocytes. The regulation of PKC on voltage-gated $Na^+$ channels has been studied on single channel level two decades ago (Reference 27). For the vertebrate brain type IIA $Na^+$ channel expressed in *Xenopus* oocytes, the open time constant was 0.26±0.05 ms, which decreased to −0.17±0.03 ms with treatment of 5 nmol/L PMA at −50 mV. Treatment of PMA also led to a reduced peak $Na^+$ current, reduced channel open probability, and prolonged time constants for channel activation. The restored peak $I_{Na}$ by inhibition of PKC may be explained by the recovery of the activation process. The connection between $NAD^+$ and PKA has been found in many studies. Extracellular $NAD^+$ binds to CD38 and results in intracellular PKA activation in human granulocytes (Reference 28) and osteoblastic cells (Reference 29). PKA activation has also found to increase the release of $NAD^+$ in canine mesenteric artery (Reference 30).

PKA phosphorylation of complex I causes an enhanced rate of NADH oxidation, reduced production of superoxide in C2C12 mouse myoblasts (Reference 31). These observations indicate a positive feedback between $NAD^+$ level and PKA activation. A second messenger for $Ca^{2+}$ regulation, cADPR, is found to be downstream of PKA activation in rat cardiomyocytes (Reference 32) and human granulocytes (Reference 28). PKA activation can increase cADPR level, which leads to an increase of cytosolic $Ca^{2+}$ concentration (References 28, 32-33). $Ca^{2+}$ stress to isolated murine cardiac mitochondrial significantly decreases the activity of complex I and III to ~30% (Reference 34). An increase of mitochondrial $Ca^{2+}$ concentration has been found to lead to a decrease of mitochondrial ROS level (Reference 35). In our unpublished work, we found that an antagonist of cADPR, 8-Br-cADPR, impaired forskolin's effect on recovering the $I_{Na}$ decreased by NADH. Therefore, extracellular $NAD^+$ could bind to CD38, lead to PKA activation, increased cADPR level and an increase of $Ca^{2+}$ concentration. Fluctuations of cytosolic $Ca^{2+}$ concentration may affect the mitochondrial $Ca^{2+}$ concentration. It is therefore possible that $NAD^+$ could regulate mitochondrial ROS level through this pathway.

It is well recognized that increasing severity of myopathy parallels sudden death risk (Reference 36), reduced $I_{Na}$ increases arrhythmic risk (Reference 37), and myopathic conditions are associated with reduced $I_{Na}$ (References 4-7). These studies suggest that myopathy is linked directly to reduced $I_{Na}$ and describe a possible mechanism whereby myopathy leads to metabolic derangements resulting in increased mitochondrial ROS production causing the reduced $I_{Na}$. Moreover, this work suggests two possible therapies to reverse the reduced $I_{Na}$ and possibly some of the arrhythmic risk associated with nonischemic cardiomyopathy.

Nonischemic cardiomyopathy was associated with NADH and mitochondrial ROS elevations, PKC activation and a concomitant decrease in $I_{Na}$. Reducing mitochondrial ROS restored $I_{Na}$. PKA activation likely participated in the signaling cascade of $NAD^+$ decreasing the mitochondrial ROS and restoring the $I_{Na}$. Since reduced $I_{Na}$ and the subsequent slow conduction velocity are thought to contribute to arrhythmic risk in cardiomyopathy, $NAD^+$ and mitochondrial anti-oxidants may have anti-arrhythmic activity in this condition.

While this invention has been described as having preferred sequences, ranges, steps, materials, structures, components, features, and/or designs, it is understood that it is capable of further modifications, uses, and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCES

The following references, including those cited in the disclosure herein, are hereby incorporated herein in their entirety by reference.
1. Bardy G H, Lee K L, Mark D B, Poole J E, Packer D L, Boineau R, Domanski M, Troutman C, Anderson J, Johnson G, McNulty S E, Clapp-Channing N, Davidson-Ray L D, Fraulo E S, Fishbein D P, Luceri R M, Ip J H. Amiodarone or an implantable cardioverter-defibrillator for congestive heart failure. *N Engl J Med* 2005; 352(3): 225-37.

2. Kamphuis H C M, de Leeuw J R J, Derksen R, Hauer R N W, Winnubst J A M. Implantable cardioverter defibrillator recipients: quality of life in recipients with and without ICD shock delivery. *Europace* 2003; 5(4):381-9.
3. Thomas S A, Friedmann E, Kao C W, Inguito P, Metcalf M, Kelley F J, Gottlieb S S. Quality of life and psychological status of patients with implantable cardioverter defibrillators. *Am J Crit Care* 2006; 15(4):389-98.
4. Valdivia C R, Chu W W, Pu J, Foell J D, Haworth R A, Wolff M R, Kamp T J, Makielski J C. Increased late sodium current in myocytes from a canine heart failure model and from failing human heart. *J Mol Cell Cardiol* 2005; 38(3):475-83.
5. Ufret-Vincenty C A, Baro D J, Lederer W J, Rockman H A, Quinones L E, Santana L F. Role of sodium channel deglycosylation in the genesis of cardiac arrhythmias in heart failure. *J Biol Chem* 2001; 276(30):28197-203.
6. Pu J, Boyden P A. Alterations of $Na^+$ currents in myocytes from epicardial border zone of the infarcted heart. A possible ionic mechanism for reduced excitability and postrepolarization refractoriness. *Circ Res* 1997; 81(1):110-9.
7. Baba S, Dun W, Boyden P A. Can PKA activators rescue $Na^+$ channel function in epicardial border zone cells that survive in the infarcted canine heart? *Cardiovasc Res* 2004; 64(2):260-7.
8. Shaw R M, Rudy Y. Ionic mechanisms of propagation in cardiac tissue: roles of the sodium and L-type calcium currents during reduced excitability and decreased gap junction coupling. *Circ Res* 1997; 81(5):727-41.
9. Liu M, Sanyal S, Gao G, Gurung I S, Zhu X, Gaconnet G, Kerchner L J, Shang L L, Huang C L H, Grace A, London B, Dudley S C, Jr. Cardiac $Na^+$ current regulation by pyridine nucleotides. *Circ Res* 2009; 105(8):737-45.
10. Liu M, Liu H, Dudley S C, Jr. Reactive oxygen species originating from mitochondria regulate the cardiac sodium channel. *Circ Res* 2010; 107(8):967-74.
11. Aon M A, Cortassa S, Marban E, O'Rourke B. Synchronized whole cell oscillations in mitochondrial metabolism triggered by a local release of reactive oxygen species in cardiac myocytes. *J Biol Chem* 2003; 278(45):44735-44.
12. Di L F, Menabo R, Canton M, Barile M, Bernardi P. Opening of the mitochondrial permeability transition pore causes depletion of mitochondrial and cytosolic $NAD^+$ and is a causative event in the death of myocytes in postischemic reperfusion of the heart. *J Biol Chem* 2001; 276(4):2571-5.
13. Silberman G A, Fan T-H, Liu H, Jiao Z, Xiao H D, Lovelock J D, Boulden B, Widder J, Fredd S, Bernstein K E, Wolska B, Dikalov S, Harrison D G, Dudley S C Jr. Uncoupled cardiac nitric oxide synthase mediates diastolic dysfunction. *Circulation* 2010; 121(4):519-28.
14. O'Connor D T, Rodrigo M, Simpson P. Isolation and culture of adult mouse cardiac myocytes. *Methods Mol Biol* 2007; 357:271-96.
15. London B, Michalec M, Mehdi H, Zhu X, Kerchner L, Sanyal S, Viswanathan P C, Pfahnl A E, Shang L L, Madhusudanan M, Baty C J, Lagana S, Aleong R, Gutmann R, Ackerman M J, McNamara D M, Weiss R, Dudley S C, Jr. Mutation in Glycerol-3-Phosphate Dehydrogenase 1-Like Gene (GPD1-L) Decreases Cardiac $Na^+$ Current and Causes Inherited Arrhythmias. *Circulation* 2007; 116(20):2260-8.
16. Landmesser U, Dikalov S, Price S R, McCann L, Fukai T, Holland S, Mitch W E, Harrison D G. Oxidation of tetrahydrobiopterin leads to uncoupling of endothelial cell nitric oxide synthase in hypertension. *J Clin Invest* 2003; 111(8):1201-9.
17. Abriel H, Kass R S. Regulation of the voltage-gated cardiac sodium channel $Na_v$ 1.5 by interacting proteins. *Trends Cardiovasc Med* 2005; 15(1):35-40.
18. Abriel H. Cardiac sodium channel $Na_v$ 1.5 and its associated proteins. *Arch Mal Coeur Vaiss* 2007; 100(9):787-93.
19. Shibata E F, Brown T L, Washburn Z W, Bai J, Revak T J, Butters C A. Autonomic regulation of voltage-gated cardiac ion channels. *J Cardiovasc Electrophysiol* 2006; 17 Suppl 1:S34-S42.
20. Akai J, Makita N, Sakurada H, Shirai N, Ueda K, Kitabatake A, Nakazawa K, Kimura A, Hiraoka M. A novel SCN5A mutation associated with idiopathic ventricular fibrillation without typical ECG findings of Brugada syndrome. *FEBS Lett* 2000; 479(1-2):29-34.
21. Brugada P, Brugada R, Brugada J. The Brugada syndrome. *Curr Cardiol Rep* 2000; 2(6):507-14.
22. Makiyama T, Akao M, Tsuji K, Doi T, Ohno S, Takenaka K, Kobori A, Ninomiya T, Yoshida H, Takano M, Makita N, Yanagisawa F, Higashi Y, Takeyama Y, Kita T, Horie M. High risk for bradyarrhythmic complications in patients with Brugada syndrome caused by SCN5A gene mutations. *J Am Coll Cardiol* 2005; 46(11):2100-6.
23. Zicha S, Maltsev V A, Nattel S, Sabbah H N, Undrovinas A I. Post-transcriptional alterations in the expression of cardiac $Na^+$ channel subunits in chronic heart failure. *J Mol Cell Cardiol* 2004; 37(1):91-100.
24. Beswick R A, Zhang H, Marable D, Catravas J D, Hill W D, Webb R C. Long-term antioxidant administration attenuates mineralocorticoid hypertension and renal inflammatory response. *Hypertension* 2001; 37(2):781-6.
25. Beswick R A, Dorrance A M, Leite R, Webb R C. NADH/NADPH oxidase and enhanced superoxide production in the mineralocorticoid hypertensive rat. *Hypertension* 2001; 38(5):1107-11.
26. Dikalova A E, Bikineyeva A T, Budzyn K, Nazarewicz R R, McCann L, Lewis W, Harrison D G, Dikalov S I. Therapeutic targeting of mitochondrial superoxide in hypertension. *Circ Res* 2010; 107(1):106-16.
27. Schreibmayer W, Dascal N, Lotan I, Wallner M, Weigl L. Molecular mechanism of protein kinase C modulation of sodium channel α-subunits expressed in *Xenopus* oocytes. *FEBS Lett* 1991; 291(2):341-4.
28. Bruzzone S, Moreschi I, Guida L, Usai C, Zocchi E, Deáflora A. Extracellular $NAD^+$ regulates intracellular calcium levels and induces activation of human granulocytes. *Biochem J* 2006; 393(3):697-704.
29. Romanello M, Padoan M, Franco L, Veronesi V, Moro L, D'Andrea P. Extracellular $NAD^+$ induces calcium signaling and apoptosis in human osteoblastic cells. *Biochem Biophys Res Commun* 2001; 285(5):1226-31.
30. Bobalova J, Mutafova-Yambolieva V N. Activation of the adenylyl cyclase/protein kinase A pathway facilitates neural release of—nicotinamide adenine dinucleotide in canine mesenteric artery. *Eur J Pharmacol* 2006; 536(1-2):128-32.
31. Technikova-Dobrova Z, Sardanelli A, Speranza F, Scacco S, Signorile A, Lorusso V, Papa S. Cyclic adenosine monophosphate-dependent phosphorylation of mammalian mitochondrial proteins: enzyme and substrate characterization and functional role. *Biochemistry* 2010; 40:13941-7.
32. Xie G H, Rah S Y, Kim S J, Nam T S, Ha K C, Chae S W, Im M J, Kim U H. ADP-ribosyl cyclase couples to cyclic AMP signaling in the cardiomyocytes. *Biochem Biophys Res Commun* 2005; 330(4):1290-8.
33. Zhang F, Jin S, Yi F, Xia M, Dewey W L, Li P L. Local production of $O_2^-$ by NAD(P)H oxidase in the sarcoplasmic reticulum of coronary arterial myocytes: cADPR-mediated Ca$^{2+}$ regulation. Cell Signal 2008; 20(4):637-44.
34. Deng N, Zhang J, Zong C, Wang Y, Lu H, Yang P, Wang W, Young G W, Wang Y, Korge P, Lotz C, Doran P, Liem D A, Apweiler R, Weiss J N, Duan H, Ping P. Phosphoproteome analysis reveals regulatory sites in major pathways of cardiac mitochondria. *Mol Cell Proteomics* 2011; 10(2): M110.000117.
35. Kohlhaas M, Liu T, Knopp A, Zeller T, Ong M F, Bohm M, O'Rourke B, Maack C. Elevated cytosolic Na$^+$ increases mitochondrial formation of reactive oxygen species in failing cardiac myocytes. *Circulation* 2010; 121(14):1606-13.
36. Epstein A E, DiMarco J P, Ellenbogen K A, Estes N A, III, Freedman R A, Gettes L S, Gillinov A M, Gregoratos G, Hammill S C, Hayes D L, Hlatky M A, Newby L K, Page R L, Schoenfeld M H, Silka M J, Stevenson L W, Sweeney M O, Smith S C, Jr., Jacobs A K, Adams C D, Anderson J L, Buller C E, Creager M A, Ettinger S M, Faxon D P, Halperin J L, Hiratzka L F, Hunt S A, Krumholz H M, Kushner F G, Lytle B W, Nishimura R A, Ornato J P, Page R L, Riegel B, Tarkington L G, Yancy C W. ACC/AHA/HRS 2008 Guidelines for Device-Based Therapy of Cardiac Rhythm Abnormalities: a report of the American College of Cardiology/American Heart Association Task Force on Practice Guidelines (Writing Committee to Revise the ACC/AHA/NASPE 2002 Guideline Update for Implantation of Cardiac Pacemakers and Antiarrhythmia Devices): developed in collaboration with the American Association for Thoracic Surgery and Society of Thoracic Surgeons. *Circulation* 2008; 117(21):e350-e408.
37. Ruan Y, Liu N, Priori S G. Sodium channel mutations and arrhythmias. *Nat Rev Cardiol* 2009; 6(5):337-48.
38. Bogdanov K Y, Vinogradova T M, Lakatta E G. Sinoatrial nodal cell ryanodine ceceptor and Na+-Ca2+ exchanger: molecular partners in pacemaker regulation. Circ Res 2001; 88:1254-8.
39. Lou Q, Fedorov V V, Glukhov A V, Moazami N, Fast V G, Efimov I R. Transmural heterogeneity and remodeling of ventricular excitation-contraction coupling in human heart failure/clinical perspective. Circulation 2011; 123:1881-90.
40. Fedorov V V, Glukhov A V, Ambrosi C M, Kostecki G, Chang R, Janks D et al. Effects of KATP channel openers diazoxide and pinacidil in coronary-perfused atria and ventricles from failing and non-failing human hearts. J Mol Cell Cardiol 2011; 51:215-25.
41. Laughner J I, Sulkin M S, Wu Z, Deng C X, Efimov I R. Three potential mechanisms for failure of high intensity focused ultrasound ablation in cardiac tissue/clinical perspective. Circ: Arrhythm Electrophysiol 2012; 5:409-16.
42. Bayly P, KenKnight B, Rogers J, Hillsley R, Ideker R, Smith W. Estimation of conduction velocity vector fields from epicardial mapping data. IEEE Trans Biomed Eng 1998; 45:563-71.
43. Glukhov A V, Fedorov V V, Kalish P W, Ravikumar V K, Lou Q, Janks D et al. Conduction remodeling in human end-stage nonischemic left ventricular cardiomyopathy/clinical perspective. Circulation 2012; 125:1835-47.
44. Murphy E, Steenbergen C. Preconditioning: the mitochondrial connection. Annu Rev Physiol 2007; 69:51-67.
45. Barth E, Stammler G, Speiser B, Schaper J. Ultrastructural quantitation of mitochondria and myofilaments in cardiac muscle from 10 different animal species including man. J Mol Cell Cardiol 1992; 24:669-81.
46. Das D K, Maulik N. Mitochondrial function in cardiomyocytes: target for cardioprotection. Curr Opin Anaesthesiol 2005; 18:77-82.
47. Duchen M R. Contributions of mitochondria to animal physiology: from homeostatic sensor to calcium signalling and cell death. J Physiol 1999; 516:1-17.
48. Ide T, Tsutsui H, Kinugawa S, Utsumi H, Kang D, Hattori N et al. Mitochondrial electron transport complex I is a potential source of oxygen free radicals in the failing myocardium. Circ Res 1999; 85:357-63.
49. Andrukhiv A, Costa A D T, West I, Garlid K D. Opening mitoKATP increases superoxide generation from complex I of the electron transport chain. Am J Physiol Heart Circ Physiol 2006; 291:H2067-H2074.
50. Eaton P. Protein thiol oxidation in health and disease: techniques for measuring disulfides and related modifications in complex protein mixtures. Free Radic Biol Med 2006; 40:1889-99.
51. Winterbourn C C. Reconciling the chemistry and biology of reactive oxygen species. Nat Chem Biol 2008; 4:278-86.
52. Santos C X C, Anilkumar N, Zhang M, Brewer A C, Shah A M. Redox signaling in cardiac myocytes. Free Radic Biol Med 2011; 50:777-93.
53. Lovelock J D, Monasky M M, Jeong E M, Lardin H A, Liu H, Patel B G et al. Ranolazine improves cardiac diastolic dysfunction through modulation of myofilament calcium sensitivity. Circ Res 2012; 110:841-50.
54. Zhou J, Shin H G, Yi J, Shen W, Williams C P, Murray K T. Phosphorylation and putative ER retention signals are required for protein kinase A-mediated potentiation of cardiac sodium current. Circ Res 2002; 91:540-6.
55. Tateyama M, Kurokawa J, Terrenoire C, Rivolta I, Kass R S. Stimulation of protein kinase C inhibits bursting in disease-linked mutant human cardiac sodium channels. Circulation 2003; 107:3216-22.

What is claimed is:

1. A method for reducing arrhythmic risk associated with cardiomyopathy characterized by an enlarged chamber, comprising the step of administering a mitochondrial targeted antioxidant to an individual in need thereof.

2. The method of claim 1, wherein the amount of antioxidant is effective to reduce arrhythmic risk.

3. The method of claim 1, wherein the antioxidant prevents or lowers reduction in sodium channel current ($I_{Na}$) by reducing or suppressing mitochondrial ROS production.

4. The method of claim 1, wherein the antioxidant is administered orally or intravenously.

5. The method of claim 1, wherein the individual is suffering from arrhythmia.

6. The method of claim 1, wherein the antioxidant comprises at least one member selected from the group consisting of a powder, a tablet, a capsule, a solution, a suspension, and an injectable formulation.

7. The method of claim 1, wherein the antioxidant comprises 2-(2,2,6,6-Tetramethylpiperidin-1-oxyl-4-ylamino)-2-oxoethyl)triphenylphosphonium chloride (MitoTEMPO).

8. A method for reducing arrhythmic risk and restoring the cardiac sodium current to a normal level in an individual with cardiomyopathy characterized by an enlarged chamber, comprising the step of administering a mitochondrial targeted antioxidant to an individual in need thereof.

9. The method of claim 8, wherein the amount of antioxidant is effective to reduce arrhythmic risk.

10. The method of claim 8, wherein the antioxidant prevents or lowers reduction in sodium channel current ($I_{Na}$) by reducing or suppressing mitochondrial ROS production.

11. The method of claim 8, wherein the antioxidant is administered orally or intravenously.

12. The method of claim 8, wherein the individual is suffering from arrhythmia.

13. The method of claim 8, wherein the antioxidant comprises at least one member selected from the group consisting of a powder, a tablet, a capsule, a solution, a suspension, and an injectable formulation.

14. The method of claim 8, wherein the antioxidant comprises 2-(2,2,6,6-Tetramethylpiperidin-1-oxyl-4-ylamino)-2-oxoethyl)triphenylphosphonium chloride (MitoTEMPO).

15. A method for reducing arrhythmic risk in an individual with cardiomyopathy characterized by an enlarged chamber and a cardiac ejection fraction of less than 50%, comprising the step of administering a mitochondrial targeted antioxidant to an individual in need thereof.

16. The method of claim 15, wherein the amount of antioxidant is effective to reduce arrhythmic risk.

17. The method of claim 15, wherein the antioxidant prevents or lowers reduction in sodium channel current ($I_{Na}$) by reducing or suppressing mitochondrial ROS production.

18. The method of claim 15, wherein the antioxidant is administered orally or intravenously.

19. The method of claim 15, wherein the individual is suffering from arrhythmia.

20. The method of claim 15, wherein the antioxidant comprises at least one member selected from the group consisting of a powder, a tablet, a capsule, a solution, a suspension, and an injectable formulation.

21. The method of claim 15, wherein the antioxidant comprises 2-(2,2,6,6-Tetramethylpiperidin-1-oxyl-4-ylamino)-2-oxoethyl)triphenylphosphonium chloride (MitoTEMPO).

* * * * *